(12) United States Patent
Crew et al.

(10) Patent No.: US 7,235,260 B2
(45) Date of Patent: Jun. 26, 2007

(54) PHARMACEUTICAL COMPOSITIONS OF A SPARINGLY SOLUBLE GLYCOGEN PHOSPHORYLASE INHIBITOR

(75) Inventors: Marshall D. Crew, Bend, OR (US); Dwayne T. Friesen, Bend, OR (US); Bruno C. Hancock, North Stonington, CT (US); Chris Macri, Belle Mead, NJ (US); James A. S. Nightingale, Bend, OR (US); Ravi M. Shankar, Groton, CT (US)

(73) Assignee: Pfizer Inc, New York, NY (US)

( * ) Notice: Subject to any disclaimer, the term of this patent is extended or adjusted under 35 U.S.C. 154(b) by 265 days.

(21) Appl. No.: 10/393,549

(22) Filed: Mar. 21, 2003

(65) Prior Publication Data

US 2003/0185891 A1    Oct. 2, 2003

Related U.S. Application Data

(62) Division of application No. 09/808,559, filed on Mar. 14, 2001, now abandoned.

(60) Provisional application No. 60/190,125, filed on Mar. 16, 2000.

(51) Int. Cl.
*A61K 9/14* (2006.01)
*A61K 9/16* (2006.01)
*A61K 9/50* (2006.01)

(52) U.S. Cl. .................. 424/489; 424/497; 424/498

(58) Field of Classification Search ............. 514/100; 424/487, 489, 488, 499, 464, 484
See application file for complete search history.

(56) References Cited

U.S. PATENT DOCUMENTS

| | | | |
|---|---|---|---|
| 4,950,484 A | 8/1990 | Olthoff et al. | 424/464 |
| 4,999,200 A | 3/1991 | Casillan | 424/480 |
| 5,085,869 A | 2/1992 | Olthoff et al. | 424/464 |
| 5,294,298 A | 3/1994 | Maesaka et al. | 159/4.01 |
| 5,464,632 A | 11/1995 | Cousin et al. | 424/465 |
| 5,490,990 A | 2/1996 | Grabowski et al. | 424/486 |
| 5,827,541 A | 10/1998 | Yarwood et al. | 424/489 |
| 5,837,292 A | 11/1998 | Dijkgraaf et al. | 424/494 |
| 5,924,216 A | 7/1999 | Takahashi | 34/374 |
| 5,955,107 A | 9/1999 | Augello et al. | 424/465 |
| 5,976,577 A | 11/1999 | Green et al. | 424/490 |
| 5,985,326 A | 11/1999 | Butler | 424/484 |
| 6,223,455 B1 | 5/2001 | Chickering, III et al. | 34/578 |
| 6,224,909 B1 | 5/2001 | Opitz et al. | 424/489 |
| 6,287,596 B1 | 9/2001 | Murakami et al. | 424/464 |
| 6,308,434 B1 | 10/2001 | Chickering, III et al. | 34/373 |
| 6,316,029 B1 | 11/2001 | Jain et al. | 424/484 |
| 2001/0027614 A1 | 10/2001 | Chickering, III et al. | 34/576 |
| 2002/0003146 A1 | 1/2002 | Long | 222/82 |
| 2002/0031547 A1 | 3/2002 | Takagi et al. | 424/464 |

FOREIGN PATENT DOCUMENTS

| | | | |
|---|---|---|---|
| EP | 0 784 974 | * | 7/1997 |
| EP | 0846464 | | 6/1998 |
| EP | 0 901 786 | * | 3/1999 |
| EP | 0901786 | | 3/1999 |
| EP | 1027886 | | 8/2000 |
| EP | 1027887 | | 8/2000 |
| EP | 1027888 | | 8/2000 |
| JP | 2000 072676 A | | 3/2000 |
| WO | WO 0147495 | | 7/2001 |
| WO | WO 0147500 | | 7/2001 |

OTHER PUBLICATIONS

Touitou, E. et al., International Journal of Pharmaceutics, vol. 11, pp. 131-148, 1982, Influence of Additives on (Hydroxyethyl) Methylcellulose Properties: Relation Between Gelation Temperature Change, Compressed Matrix Integrity and Drug Release Profile.
Catellani, P. L. et al., International Journal of Pahrmaceutics, vol. 51, pp. 63-66, 1989, "Tablet Water Uptake and Disintegration Force Measurements".
Colombo, P. et al., vol. 73, No. 5, pp. 701-705, May 1984, "Disintegrating Force as a New Formulation Parameter".
Massimo, G. et al., vol. 5(2), pp. 163-169, 2000, "Disintegration Propensity of Tablets Evaluated by Means of Disintegrating Force Kinetics".
Sinko, C. M. et al., International Journal of Pharmaceutics, vol. 114, pp. 85-93, 1995, "The Identification of Percolation and Mechanical Thresholds During the Compaction of Hydroxypropyl Methylcellulose: Comparison to Thresholds Determined from Out-of-Die Indentation Experiments".
Berman, J. et al., Drug Development and Industrial Pharmacy, vol. 20(5), pp. 731-755 (1994), "Scale-Up of a Spray Dry Tablet Granulation Process: Thermodynamic Considerations".
Yu, L., Advanced Drug Delivery Reviews, vol. 48, pp. 27-42, 2000, "Amorphous Pharmaceutical Solids: Preparation, Characterization and Stabilization".
Christensen, K. L. et al., International Journal of Pharmaceutics, vol. 212, pp. 195-202, 2001, "Technical Optimisation of Redispersible Dry Emulsions".
Yoo, S. D. et al., Drug Development and Industrial Pharmacy, vol. 26(1), pp. 27-34, 2000, "Bioavailability of Itraconazole in Rats and Rabbits After Administration of Tablets Containing Solid Dispersion Particles".
H. Bauer, M. Bartels, E. Schwarz, and P.C. Schmidt, Particle Design by Surface Modifications: Spray-Drying and Co-Granulation of Mannitol/Sorbitol Mixtures, *S.T.P. Pharma Sci.*, 2001, vol. 11, No. 3, pp. 203-209.
Pharmaceutics: The Science of Dosage Form Design, pp. 156-158 (1988).

\* cited by examiner

*Primary Examiner*—Michael G. Hartley
*Assistant Examiner*—Blessing Fubara
(74) *Attorney, Agent, or Firm*—Gregg C. Benson; James T. Jones

(57) ABSTRACT

Pharmaceutical compositions of a particularly effective sparingly soluble glycogen phosphorylase inhibitor are disclosed, as well as methods of making such compositions and dosage forms from such compositions.

9 Claims, No Drawings

PHARMACEUTICAL COMPOSITIONS OF A SPARINGLY SOLUBLE GLYCOGEN PHOSPHORYLASE INHIBITOR

This application claims priority under 35 U.S.C. §120 to U.S. Ser. No. 09/808,559, filed Mar. 14, 2001, which claims priority to Provisional Application No. 60/190,125 filed Mar. 16, 2000.

BACKGROUND OF THE INVENTION

Type 2 diabetes is often treated by drugs designed to suppress hepatic glucose production. One class of drugs having this capability are drugs that inhibit glycogen phosphorylase, the enzyme which mediates the breakdown of glycogen. Such glycogen phosphorylase inhibitors (GPIs) inhibit the liver's production of glucose by inhibiting this enzyme's ability to catalyze glycogonolysis, or the breakdown of the glucose polymer glycogen. A particularly effective GPI is 5-chloro-1H-indole-2-carboxylic acid [(1S)-benzyl-(2R)-hydroxy-3-((3R,4S)-dihydroxy-pyrrolidin-1-yl-)-3-oxypropyl]amide, having the structure

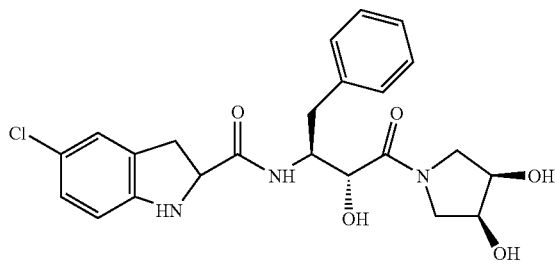

and, for ease of reference, hereinafter referred to as Drug A. See PCT Application WO 96/39385 A1.

Although most known classes of GPIs have relatively high aqueous solubility and correspondingly high bioavailability when dosed orally, Drug A is a sparingly soluble drug, the lowest energy crystalline form of which has an aqueous solubility of from about 0.06 to about 0.08 mg/mL. Because of such low aqueous solubility, when tested in vitro Drug A has low maximum concentration ($c_{max}$) and area under the concentration vs. time curve (AUC) values in a given environment of use. In addition, when the lowest energy crystalline form of the drug is tested in vivo by orally dosing, the $c_{max}$ of Drug A in the blood plasma, its AUC and its relative bioavailability are all low. Thus, it would be desirable to enhance the relative bioavailability of Drug A.

BRIEF SUMMARY OF THE INVENTION

It has been found that pharmaceutical compositions that combine Drug A in a variety of forms with a concentration-enhancing polymer can enhance the aqueous concentration in a use environment and the bioavailability of Drug A. For a given use environment, such pharmaceutical compositions include (1) an amorphous solid dispersion of Drug A in the concentration-enhancing polymer; (2) an amorphous solid dispersion of Drug A and additional concentration-enhancing polymer, the composition being either preformed or formed in situ; and (3) an amorphous form of Drug A and a concentration-enhancing polymer, the composition being either preformed or formed in situ. Such compositions provide in an aqueous environment of use or in blood plasma or serum, an AUC value for Drug A that is at least 1.25-fold, and a $c_{max}$ of Drug A that is at least 1.25-fold, and more typically 3- to 10-fold that of a control composition comprising an equivalent quantity of crystalline Drug A alone in the lowest energy crystalline form presently known to the inventors. In terms of concentration, such compositions exhibit an aqueous solubility of at least 0.10 mg/mL, preferably at least 0.16 mg/mL, and more preferably at least 0.24 mg/mL. Such compositions can be used in virtually any device for administering the drug in vivo, including immediate release and controlled release, i.e., sustained and delayed release dosage forms.

Thus, a primary aspect of the present invention is a pharmaceutical composition comprising amorphous solid dispersions of Drug A in a concentration-enhancing polymer.

A closely related aspect of the present invention pertains to methods for forming such amorphous solid dispersions and to techniques for processing the dispersions once made.

Another aspect of the present invention comprises a pharmaceutical composition comprising an amorphous solid dispersion of Drug A and additional concentration-enhancing polymer, the composition being formed either outside the environment of use or inside the environment of use (i.e., in situ).

Another aspect of the present invention is a pharmaceutical composition comprising amorphous Drug A and a concentration-enhancing polymer, the composition being formed either outside the environment of use or inside the environment of use (i.e., in situ).

Another aspect of the present invention comprises a dosage form based upon such pharmaceutical compositions of Drug A, including both immediate release and controlled release forms, the latter including both delayed and sustained release forms.

Yet another aspect of the present invention comprises a method of treating a person in need of GPI therapy comprising administering to said person a pharmaceutical composition of the present invention.

DETAILED DESCRIPTION OF PREFERRED EMBODIMENTS

The pharmaceutical compositions of the present invention are fabricated in three distinct forms:

(1) an amorphous solid dispersion of Drug A in a "concentration-enhancing polymer" (defined below);

(2) an amorphous solid dispersion of Drug A and additional concentration-enhancing polymer; and (3) amorphous Drug A and a concentration-enhancing polymer.

As to forms (2) and (3), the component containing Drug A may be combined with the concentration-enhancing polymer component in a dosage form in conventional fashion or it may be co-administered to the environment of use separately from the concentration-enhancing polymer component, but sufficiently close in time that the two components are in the environment of use together so that the enhancement of the concentration of Drug A takes place in the environment of use.

All three forms of the pharmaceutical compositions of the present invention meet the in vitro or in vivo solubility tests disclosed herein.

Each of these three forms may include solubilizers and excipients, may be formed into granules for processing, may be incorporated into water-erodible matrices for delivery by erosion or diffusion, or may be incorporated into water-soluble or water-swellable cores and coated for delivery by osmotically driven mechanisms. All such forms may be formulated into any known dosage form and designed for immediate release of Drug A, delayed release, controlled release, or any combination of these two types of release. Such dosage forms may be used for the administration of Drug A to a person in need of GPI therapy.

Thus, each of the pharmaceutical compositions of the present invention are made from two key components: (1) Drug A, and (2) at least one concentration-enhancing polymer. Each of these components is discussed below.

Drug A

Drug A is a particularly effective GPI. It can be prepared according to the methods disclosed in PCT Application WO 96/39385 A1, the pertinent disclosure of which is incorporated herein by reference. Drug A, in pure form, can be isolated in various crystalline forms and in amorphous form. Although amorphous forms can vary in their physical nature, by "amorphous" is meant simply that a major portion of Drug A is in a non-crystalline state. As used herein, the phrase "a major portion" of Drug A means that at least 60% of the GPI in the composition is in the amorphous form, rather than the crystalline form. Preferably, Drug A in the composition is "substantially amorphous." As used herein, "substantially amorphous" means that the amount of Drug A in crystalline form does not exceed 25%. The amount of crystalline Drug A may be determined by generally accepted analytical methods such as Scanning Electron Microscope (SEM), Differential Scanning Calorimetry (DSC) or Powder X-ray Diffraction (PXRD). Preferably, essentially all (>90%) of Drug A is in the amorphous state, or stated conversely, the amount of crystalline Drug A does not exceed 10%.

Drug A is generally prepared as its lowest energy crystalline state known, characterized by a melting point of about 238° C. and a solubility in distilled water or phosphate buffered solution (PBS) of from about 0.06 to about 0.08 mg/mL at 37° C. Drug A is nonionic over the physiologically relevant pH range of 1 to 8 and, as a result, has approximately the same solubility in dilute aqueous solutions with pH values in this range. Amorphous forms of Drug A as well as any crystalline states that may exist besides the lowest energy crystalline state known mentioned above generally will have higher aqueous solubility than the lowest energy crystalline state known, generally referred to herein as the "crystalline state."

The Concentration-Enhancing Polymer

The second key component used in forming the pharmaceutical compositions of the present invention is polymeric, pharmaceutically acceptable, inert, aqueous-soluble, and concentration-enhancing.

By "polymeric" is meant that the material is made up of a series of similar repeat units ranging in number from 5 to 10 up to many thousands. The repeat units essentially all may be the same, as would be the case for a polymer such as polyvinylpyrrolidone, or they may vary as would be the case for a substituted cellulosic polymer.

By "pharmaceutically acceptable" is meant that the polymer does not adversely affect the subject or patient when administered appropriately. By "inert" is meant not adversely reactive or bioactive, yet still having concentration-enhancing capacity and capable of enhancing Drug A's bioavailability.

Such polymers are "aqueous-soluble" in the sense that they are sufficiently soluble ($\geq 0.1$ mg/mL) in at least a portion of the 1 to 8 pH range that they exhibit a "concentration-enhancing" property with respect to Drug A. By "concentration-enhancing" is meant that, following introduction of the polymer and a "high energy form" of Drug A into an aqueous environment of use, as compared to a control consisting of an equivalent quantity of Drug A in its most thermodynamically stable, lowest energy crystalline form but without the polymer, those objective measures of concentration that correspond to enhanced bioavailability for either in vitro or in vivo testing and set forth below are met.

By "high energy form of Drug A" is meant any form that has an aqueous solubility of at least 1.25-fold that of the lowest energy crystalline form known, or at least 0.10 mg/mL. This includes any substantially amorphous form of Drug A, including amorphous Drug A alone; Drug A dispersed in the concentration-enhancing polymer; Drug A dispersed in another matrix material; and any crystalline form of Drug A that has an aqueous solubility of at least 0.10 mg/mL.

The compositions comprising Drug A and concentration-enhancing polymer provide enhanced concentration of Drug A in in vitro dissolution tests. It has been determined that enhanced drug concentration in in vitro dissolution tests in Model Fasted Duodenal (MFD) or Phosphate Buffered Saline (PBS) solution is a good indicator of in vivo performance and bioavailability. In particular, a composition of the present invention can be dissolution-tested by adding it to MFD or PBS solution and agitating to promote dissolution. Exemplary MFD and PBS solutions are set forth in the Examples herein. Preferably, the composition of the present invention provides a $c_{max}$ of dissolved Drug A that is at least 1.25-fold the equilibrium concentration of a control composition comprising an equivalent quantity of Drug A but free from the polymer. As used herein, $c_{max}$ is the maximum concentration of dissolved Drug A in the test medium observed by analysis of the test medium. In other words, if the equilibrium concentration of dissolved Drug A provided by the control composition is 0.08 mg/mL, then a composition of the present invention provides a $c_{max}$ of at least 0.10 mg/mL.

The control composition is conventionally undispersed Drug A alone (e.g., typically, crystalline Drug A alone in its most thermodynamically stable, lowest energy crystalline form). For the embodiment of this invention that comprises Drug A in an amorphous state and one or more concentration-enhancing polymers, the control may be amorphous Drug A alone or amorphous Drug A plus a weight of inert diluent equivalent to the weight of polymer in the test composition. More preferably, the $c_{max}$ of dissolved Drug A achieved with the compositions of the present invention exceeds the equilibrium drug concentration of the control by at least 2-fold, and most preferably of at least 3-fold, meaning that the $c_{max}$ is at least 0.16 mg/mL and 0.24 mg/mL, respectively.

Alternatively, in an in vitro dissolution test reflected by a plot of dissolved Drug A concentration versus time the compositions of the present invention provide an Area Under the Curve (AUC) for any period of at least 90 minutes between the time of introduction into the use environment and about 270 minutes following introduction that is at least 1.25-fold that of a control composition comprising an equivalent quantity of Drug A alone. The determination of AUCs is a well-known procedure and is described, for example, in Welling, "Pharmacokinetics Processes and Mathematics," ACS Monograph 185 (1986).

A typical test to evaluate enhanced drug concentration can be conducted by (1) suspending a sufficient quantity of control composition, typically Drug A alone, in the in vitro test medium, typically either MFD or PBS solution, to achieve the equilibrium concentration of dissolved Drug A; (2) suspending a sufficient quantity of test composition (e.g., the amorphous state Drug A and polymer or a dispersion of Drug A in polymer) in an equivalent test medium, such that if all Drug A is dissolved, the theoretical concentration of Drug A would exceed the equilibrium concentration of "dissolved Drug A" by at least 2-fold; and (3) determining whether the measured $c_{max}$ of the test composition in the test medium is at least 1.25-fold that of the equilibrium concentration of the control composition.

The concentration of "dissolved Drug A" is typically measured as a function of time by sampling the test medium, measuring the concentration of "dissolved Drug A" and plotting concentration versus time so that the $c_{max}$ can be ascertained. To avoid particulates of Drug A (e.g., undissolved) which would give an erroneous determination, the test solution is either filtered or centrifuged. "Dissolved Drug A" is typically taken as that material that either passes a 0.45 µm syringe filter or, alternatively, the material that remains in the supernatant following centrifugation. Filtration can be conducted using a 13 mm, 0.45 µm polyvinylidine difluoride syringe filter sold by Scientific Resources under the trademark TITAN®.

Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (±10–40%) than that obtained with the filter specified above but will still allow identification of preferred dispersions. It is recognized that this definition of "dissolved Drug A" encompasses not only monomeric solvated Drug A molecules but also a wide range of species such as polymer/Drug A assemblies that have submicron dimensions, Drug A aggregates, aggregates of mixtures of polymer and Drug A, micelles, polymeric micelles, colloidal particles or nanocrystals, polymer/Drug A complexes, and other such Drug A-containing species that are present in the filtrate or supernatant in the specified dissolution test.

Alternatively, compositions of the present invention, when dosed orally to a human or other animal, provide an AUC in Drug A concentration in the blood (plasma or serum) that is at least 1.25-fold that observed when a control composition comprising an equivalent quantity of Drug A is dosed alone (in the absence of the concentration-enhancing polymer), which is equivalent to the compositions having a relative bioavailability of 1.25 as compared to such a control composition.

Relative bioavailability of Drug A in the compositions of the present invention can be tested in vivo in animals or humans using conventional methods for making such a determination. An in vivo test, such as a crossover study, may be used to determine whether a composition of Drug A and polymer provides an enhanced Drug A concentration in the blood (serum or plasma) versus time Area Under the Curve (AUC) for a test subject dosed with the test composition relative to the Drug A concentration in the blood versus time AUC for a test subject dosed with a control composition comprised of crystalline or amorphous Drug A but no polymer as described above.

In an in vivo crossover study a "test composition" of Drug A and polymer is dosed to half a group of 12 or more humans and, after an appropriate washout period (e.g., one week) the same subjects are dosed with a "control composition" that comprises an equivalent quantity of Drug A as the test composition. The other half of the group is dosed with the control composition first, followed by the test composition. The relative bioavailability is measured as the concentration in the blood (serum or plasma) versus time Area Under the Curve (AUC) provided by the test composition determined for each group divided by the AUC in the blood provided by the control composition. Preferably, this test/control ratio is determined for each subject, and then the ratios are averaged over all subjects in the study.

In vivo determinations of AUC can be made by plotting the serum or plasma concentration of drug along the ordinate (y-axis) against time along the abscissa (x-axis). Generally, the values for AUC represent a number of values taken from all of the subjects in a patient test population, averaged over the entire test population. A preferred embodiment of the invention is one in which the relative bioavailability of the test composition is at least 1.25 relative to a control composition comprising Drug A but with no polymer. An even more preferred embodiment of the invention is one in which the relative bioavailability of the test composition is at least 2.0 relative to a control composition of Drug A but with no polymer present.

Polymers suitable for use with the present invention may be cellulosic or non-cellulosic. The polymers may be neutral or ionizable in aqueous solution. Of these, ionizable and cellulosic polymers are preferred, with ionizable cellulosic polymers being more preferred.

A preferred class of polymers comprises polymers that are "amphiphilic" in nature, meaning that the polymer has hydrophobic and hydrophilic portions. Hydrophobic groups may comprise groups such as aliphatic or aromatic hydrocarbon groups. Hydrophilic groups may comprise either ionizable or non-ionizable groups that are capable of hydrogen bonding such as hydroxyls, carboxylic acids, esters, amines or amides.

Amphiphilic and/or ionizable polymers are preferred because it is believed that such polymers may tend to have relatively strong interactions with Drug A and may promote the formation in the use environment of the various types of polymer/drug assemblies described previously. In addition, the repulsion of the like charges of the ionized groups of such polymers may serve to limit the size of the polymer/drug assemblies to the nanometer or submicron scale. For example, while not wishing to be bound by a particular theory, such polymer/drug assemblies may comprise hydrophobic Drug A clusters surrounded by the polymer with the polymer's hydrophobic regions turned inward towards Drug A and the hydrophilic regions of the polymer turned outward toward the aqueous environment. Alternatively, the ionized functional groups of the polymer may associate, for example, via hydrogen bonds, with polar groups of Drug A. In the case of ionizable polymers, the hydrophilic regions of the polymer would include the ionized functional groups. Such drug/polymer assemblies in solution may well resemble charged polymeric micellar-like structures. In any case, regardless of the mechanism of action, the inventors have observed that such amphiphilic polymers, particularly ionizable cellulosic polymers, have been shown to improve the concentration of Drug A in aqueous solution relative to control compositions free from such polymers.

One class of polymers suitable for use with the present invention comprises neutral non-cellulosic polymers. Exemplary of such polymers are polyvinyl alcohols that have at least a portion of their repeat units in the unhydrolyzed (vinyl acetate) form, polyvinyl alcohol polyvinyl acetate copolymers, polyethylene glycol/polypropylene glycol copolymers, polyvinyl pyrrolidone, polyethylene polyvinyl alcohol copolymers, and chitosan.

Another class of polymers suitable for use with the present invention comprises ionizable non-cellulosic polymers. Exemplary polymers include: vinyl polymers and copolymers having substituents of hydroxyl, alkylacyloxy, and cyclicamido; carboxylic acid-functionalized polymethacrylates and carboxylic acid functionalized polyacrylates such as the EUDRAGITS® manufactured by Rohm Tech Inc., of Malden, Mass.; amine-functionalized polyacrylates and polymethacrylates; proteins; and carboxylic acid functionalized starches such as starch glycolate.

Non-cellulosic polymers that are amphiphilic are copolymers of a relatively hydrophilic and a relatively hydrophobic monomer. Examples include acrylate and methacrylate copolymers. Exemplary commercial grades of such copolymers include the EUDRAGITS, which are copolymers of methacrylates and acrylates.

A preferred class of polymers comprises ionizable and neutral cellulosic polymers with at least one ester- and/or ether-linked substituent in which the polymer has a degree of substitution of at least 0.05 for each substituent. It should be noted that in the polymer nomenclature used herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

It should also be noted that a polymer name such as "cellulose acetate phthalate" (CAP) refers to any of the family of cellulosic polymers that have acetate and phthalate groups attached via ester linkages to a significant fraction of the cellulosic polymer's hydroxyl groups. Generally, the degree of substitution of each substituent group can range from 0.05 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been phthalate substituted, the phthalate, degree of substitution is 3. Also included within each polymer family type are cellulosic polymers that have additional substituents added in relatively small amounts that do not substantially alter the performance of the polymer.

Amphiphilic cellulosics may be prepared by substituting the cellulosic at any or all of the 3 hydroxyl substituents present on each saccharide repeat unit with at least one relatively hydrophobic substituent. Hydrophobic substituents may be essentially any substituent that, if substituted to a high enough level or degree of substitution, can render the cellulosic polymer essentially aqueous insoluble. Hydrophilic regions of the polymer can be either those portions that are relatively unsubstituted, since the unsubstituted hydroxyls are themselves relatively hydrophilic, or those regions that are substituted with hydrophilic substituents. Examples of hydrophobic substituents include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate. Hydrophilic groups include ether- or ester-linked nonionizable groups such as the hydroxy alkyl substituents hydroxyethyl, hydroxypropyl, and the alkyl ether groups such as ethoxyethoxy or methoxyethoxy. Particularly preferred hydrophilic substituents are those that are ether- or ester-linked ionizable groups such as carboxylic acids, thiocarboxylic acids, substituted phenoxy groups, amines, phosphates or sulfonates.

One class of cellulosic polymers comprises neutral polymers, meaning that the polymers are substantially nonionizable in aqueous solution. Such polymers contain nonionizable substituents, which may be either ether-linked or ester-linked. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable groups include: alkyl groups, such as acetate, propionate, butyrate, etc.; and aryl groups such as phenylate, provided, however, especially when aryl groups are included, that the polymer include sufficient hydrophilic substituents that the polymer has at least some water solubility at pH 1 to 8.

Exemplary non-ionizable cellulosic polymers that may be used as the polymer include: hydroxypropyl methyl cellulose acetate, hydroxypropyl methyl cellulose (HPMC), hydroxypropyl cellulose (HPC), methyl cellulose, hydroxyethyl methyl cellulose, hydroxyethyl cellulose acetate, and hydroxyethyl ethyl cellulose.

A preferred set of neutral cellulosic polymers are those that are amphiphilic. Exemplary polymers include hydroxypropyl methyl cellulose and hydroxypropyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer.

Another class of cellulosic polymers comprises polymers that are at least partially ionizable at physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid; thiocarboxylic acids, such as thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester linked ionizable substituents include: carboxylic acids, such as succinate, citrate, phthalate, terephthalate, isophthalate, trimellitate, and the various isomers of pyridinedicarboxylic acid; thiocarboxylic acids, such as thiosuccinate; substituted phenoxy groups, such as aminosalicylic acid; amines, including natural or synthetic amino acids such as alanine and phenylanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous-soluble at least at pH values where any ionizable groups are ionized. In some cases, the aromatic group may itself be ionizable such as in the case of phthalate or trimellitate substituents.

Exemplary ionizable cellulosic polymers that are at least partially ionized at physiologically relevant pHs that may be used as the dispersion polymer include: hydroxypropyl methyl cellulose acetate succinate (HPMCAS), hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate (HPMCP), hydroxyethyl methyl cellulose acetate succinate, hydroxyethyl methyl cellulose acetate phthalate, carboxyethyl cellulose, carboxymethyl cellulose, cellulose acetate phthalate (CAP), methyl cellulose acetate phthalate, ethyl cellulose acetate phthalate, hydroxypropyl cellulose acetate phthalate, hydroxypropyl methyl cellulose acetate phthalate, hydroxypropyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, ethyl picolinic acid cellulose acetate, carboxymethyl cellulose, carboxymethyl cellulose acetate, and ionizable salts of all the foregoing.

Exemplary cellulosic polymers that meet the definition of amphiphilic, having hydrophilic and hydrophobic regions include polymers such as CAP and CAT where the cellulosic repeat units that have one or more acetate substituents are hydrophobic relative to those that have no acetate substituents or have one or more ionized phthalate or trimellitate substituents.

A particularly desirable subset of cellulosic ionizable polymers are those that possess both a carboxylic acid functional aromatic substituent and an alkylate substituent and thus are amphiphilic. Exemplary polymers include cellulose acetate phthalate, methyl cellulose acetate phthalate, ethyl cellulose acetate phthalate, hydroxypropyl cellulose acetate phthalate, hydroxypropyl methyl cellulose phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Another particularly desirable subset of cellulosic ionizable polymers are those that possess a non-aromatic carboxylate substituent. Exemplary polymers include hydroxypropyl methyl cellulose acetate succinate, hydroxypropyl methyl cellulose succinate, hydroxypropyl cellulose acetate succinate, hydroxyethyl methyl cellulose acetate succinate, hydroxyethyl methyl cellulose succinate, and hydroxyethyl cellulose acetate succinate.

Especially preferred polymers are methyl cellulose acetate phthalate, hydroxypropyl cellulose acetate phthalate, cellulose acetate terephthalate, cellulose acetate isophthalate, hydroxypropyl methyl cellulose acetate succinate, hydroxypropyl methyl cellulose phthalate, cellulose acetate phthalate, and cellulose acetate trimellitate. Most preferred polymers are hydroxypropyl methyl cellulose acetate succinate, hydroxypropyl methyl cellulose phthalate, cellulose acetate phthalate, and cellulose acetate trimellitate.

While a wide range of amphiphilic polymers have concentration-enhancing properties, those cited above as being preferred generally provide greater enhancements in $c_{max}$, AUC and bioavailability relative to the other polymers of the present invention. For example, it has been found that compositions that utilize the most preferred concentration-enhancing polymers provide a $c_{max}$ in an environment of use that is 4-fold to 30-fold that of a control composition.

It should also be noted that while a few of the concentration-enhancing polymers listed above are commonly used in pharmaceutical formulations, their conventional uses are not for concentration enhancement and therefore they are normally used at lower levels than required to observe substantial concentration enhancement. For example, HPMC is a commonly used binder in pharmaceutical formulations and CAP is commonly used as an enteric coating for pharmaceutical tablets. However, in such uses the amount of polymer used in a tablet is generally much less than would be used to enhance the concentration of Drug A. In addition, such polymers are conventionally used with crystalline drug while, for such polymers to provide concentration enhancement the drug must be in a concentration-enhanced form such as an amorphous state or an amorphous dispersion.

While specific polymers have been discussed as being suitable for use in the mixtures of the present invention, blends of such polymers may also be suitable. Thus the term "polymer" is intended to include blends of polymers in addition to a single species of polymer. For example, when it is desirable to combine two concentration-enhancing polymers such as PVP (a nonionic vinyl polymer that is highly water-soluble) and HPMCAS (an ionic cellulosic that has a high glass transition temperature ($T_g$) of 118° C.), they can be combined in a wide variety of ways. For example, a solid amorphous dispersion of Drug A and both polymers can be combined such that they are as homogeneous as possible by, for example, dissolving all three materials in a solvent and then solidifying by precipitation in a non-solvent or by evaporation of the solvent. Alternatively, a dispersion may be formed from Drug A with a first concentration-enhancing polymer, followed by dry- or wet-blending a second concentration-enhancing polymer with the dispersion. The second concentration-enhancing polymer may also be added as a coating or as a wet-granulating material.

Dispersions of Drug and Concentration-Enhancing Polymer

A first aspect of this invention comprises solid amorphous dispersions of Drug A and one or more aqueous-soluble, concentration-enhancing polymers. Broadly, a major portion ($\geq 60\%$) of Drug A is in amorphous, as opposed to crystalline, form. Preferably, Drug A in such dispersions is substantially amorphous in the sense that at least 75% of Drug A is in a non-crystalline state (equivalent to 25% or less of Drug A being in a crystalline state). As previously mentioned, the amorphous nature of Drug A in the dispersion can be demonstrated, for example, by DSC or SEM analysis or by PXRD. Preferably, essentially all of Drug A is amorphous in the sense that less than 10% of Drug A in the dispersion is in the crystalline state.

Although, as discussed below, amorphous Drug A and the aqueous-soluble concentration-enhancing polymer can be a simple physical mixture, it is generally preferred that Drug A be at least partially dispersed in the concentration-enhancing polymer. Even more preferably, Drug A is as homogeneously dispersed as possible in the concentration-enhancing polymer. One method to determine whether Drug A is relatively homogeneously dispersed in the concentration-enhancing polymer is by DSC analysis. Generally, the observation of a single $T_g$ for the dispersion that is between that of the polymer alone and that of Drug A alone is an indication of good homogeneity. Typically, for a non-homogeneous dispersion, such as a physical blend of amorphous Drug A and polymer, there will be two $T_g$s-one for Drug A and one for the polymer. Although dispersions may be prepared by any of the methods described below, some methods noted below are preferred in that they result in more homogeneous dispersions, and in a higher fraction of Drug A being in the amorphous state.

Methods of Forming Dispersion

The amorphous solid dispersion of drug may be prepared by any of the known ways for doing so, including, for example, by melt fusion, by melt congealing, by lyophilization, by extended mechanical processing such as by trituration, or in a twin-screw extruder or in a ball mill, or by solvent processing. When the dispersion is made by mechanical means such as by ball milling or extrusion, a major portion ($\geqq 60\%$) of the drug is typically in an amorphous state, with the remaining portion in a crystalline state. However, in some cases mechanical processing may lead to larger fractions of Drug A being amorphous. When prepared by solvent processing, a major portion of the drug is in an amorphous state, usually substantially all (>75%) is in an amorphous state, and often essentially all (>90%) of the drug is in an amorphous state. By "amorphous state" is meant the drug may be present in the dispersion in any non-crystalline state such as any of the following three broad classes of forms: (a) in discrete, drug-rich domains; (b) homogeneously distributed therein, i.e., a solid solution; or (c) any state or combination of states between the extremes of (a) and (b).

In solvent processing, a homogeneous solution of solvent, drug and the concentration-enhancing polymer is formed, alone or along with other excipients that may or may not be dissolved, followed by solvent removal by precipitation or evaporation. Because solvent processing permits formation of homogeneous amorphous solid dispersions, it is the preferred class of fabrication methods for forming the amorphous solid dispersion of Drug A. All of the following forms of solvent processing are useful in forming the solid dispersion form of the pharmaceutical composition of the present invention: spray-drying, spray-coating, evaporation, rotovaporation, fluid bed drying, precipitation and combinations thereof. Precipitation is typically induced by contacting the drug/dispersion polymer solution with a non-solvent such as water, a liquid hydrocarbon or super-critical $CO_2$.

A preferred method of forming the dispersion is by dissolving the drug and dispersion polymer in a common solvent; then removing the solvent by spray-drying or spray-coating. Spray-drying and spray-coating processes and equipment are described generally in *Perry's Chemical Engineers' Handbook*, pages 20–54 to 20–57 (6th Ed. 1984). More details on spray-drying processes and equipment are reviewed by Marshal in 50 *Chem. Eng. Prog. Monogr.* series 2 (1954).

The terms "spray-drying" and "spray-coating" in connection with the present invention are used conventionally and broadly refer to processes involving breaking up liquid mixtures into small droplets (atomization) and rapidly removing solvent from the mixtures in a vessel such as a spray-drying apparatus or a fluidized bed- or pan-coater where there is a strong driving force for evaporation of solvent from the droplets. In the case of spray-coating, the droplets impinge on a particle, bead, pill, tablet, or capsule, resulting in a coating comprising the solid amorphous dispersion. Spray-coating may also be conducted on a metal, glass or plastic surface and the coated layer may subsequently be removed and milled to the desired particle size. In the case of spray-drying, the droplets generally dry prior to impinging on a surface, thus forming particles of solid amorphous dispersion on the order of 1 to 200 micrometers in diameter. The strong driving force for solvent evaporation is generally provided by maintaining the partial pressure of solvent in the spray-drying apparatus well below the vapor pressure of the solvent at the temperature of the drying droplets. This is accomplished by either (1) maintaining the pressure in the spray-drying apparatus at a partial vacuum (e.g., 0.01 to 0.50 atm); (2) mixing the liquid droplets with a warm drying gas; or (3) both (1) and (2). For example, a solution of drug and a dispersion polymer such as HPMCAS in acetone may be suitably spray-dried by spraying the solution at a temperature of 50° C. (the vapor pressure of acetone at 50° C. is about 0.8 atm) into a chamber held at 0.01 to 0.2 atm total pressure by connecting the outlet to a vacuum pump. Alternatively, such a solution may be sprayed into a chamber where it is mixed with nitrogen gas at a temperature of 80° C. to 250° C. and pressure of 1.0 to 1.2 atm.

Generally, the temperature and flow rate of the drying gas is chosen so that dispersion polymer/drug solution droplets are dry enough by the time they reach the wall of the apparatus that they are essentially solid, so that they form a fine powder and do not stick to the apparatus wall. The actual length of time to achieve this level of dryness depends on the size of the droplets. Droplet sizes generally range from 1 to 500 µm in diameter, with 5 to 100 µm being more typical. The large surface-to-volume ratio for the droplets and the large driving force for evaporation of solvent generally leads to actual drying times of a few seconds or less, and more typically substantially less than a second. For some mixtures of drug/dispersion polymer/solvent this rapid drying generally leads to a more uniform, homogeneous composition, as opposed to the generally less desirable separation into drug-rich and polymer-rich phases. Such dispersions having a homogenous composition can be considered solid solutions and may be supersaturated in drug.

However, as described below, separation of Drug A from the dispersion polymer to form essentially a physical blend of particles or domains of amorphous Drug A and the concentration-enhancing polymer can also have good performance and also forms a part of this invention. As a result, solidification times can be quite long-even in excess of an hour as might occur by bulk evaporation of solvent from a stirred or agitated vessel. However, preferably, solidification times should be less than 100 seconds, preferably less than 20 seconds, and more preferably less than 1 second. In general, to achieve such rapid solidification of the drug/dispersion polymer solution, it is preferred that the solution be spray-dried or spray-coated by the formation of droplets during the spray-drying or spray-coating process that are less than 500 μm. The so-formed solid particles resulting from solidification of these droplets generally tend to be 1 to 200 μm in diameter.

Following solidification, the solid particles may remain in the spray-drying chamber for additional time, evaporating more solvent. Generally, when the dispersion exits the spray-drying apparatus, its residual solvent content should be less than 10 wt % and preferably less than 2 wt %.

The solution spray-dried to form the solid amorphous dispersion can be quite simple, containing only Drug A, one or more concentration-enhancing polymers and one or more solvents. In such cases, the solids content of the spray-drying solution is generally in the range of from 1 to 30 wt %, and more preferably from 5 to 20 wt %. Following spray-drying and, if required, a secondary drying step, the resulting dispersion is essentially free of solvent and thus consists primarily of Drug A and one or more concentration-enhancing polymers.

When the dispersion is the only source of concentration-enhancing polymer in the dosage form, the Drug A content of the dispersion is generally 5 to 75 wt %. Preferably, to limit the total mass of the dosage form, the Drug A content is at least 15 wt %, although good relative bioavailability is generally expected at even very low drug loadings (Drug A content of 1 to 15 wt %). In addition, when concentration-enhancing polymer other than in the dispersion is included in the dosage form, rather surprisingly it has been found that the Drug A content of the dispersion can be quite high, approaching 100%, since dispersions containing 99 wt % Drug A have shown marked enhancement of Drug A concentration.

When the concentration-enhancing polymer is HPMCAS, typically 5 to 10 wt % Drug A and 5 to 10 wt % HPMCAS are dissolved either in pure acetone or acetone containing up to 10 wt % water. For example, to form a dispersion of 50% Drug A and 50% HPMCAS, 6.5 wt % Drug A and 6.5 wt % HPMCAS are dissolved in a solvent composed of 95% acetone and 5% water. Thus, the solution composition is 6.5 wt % Drug A, 6.5 wt % HPMCAS, 82.65 wt % acetone and 4.35 wt % water. It was found that Drug A was stable in this solution for up to 7 days' storage at ambient temperatures in a stainless steel container. Solids contents in such solutions have been increased to up to 15 wt % and have been successfully spray-dried with good results.

Other excipients may be added to the spray solution, either co-dissolved in the solvent along with the drug and dispersion polymer or suspended in the solution to form a slurry. Such exdipients may include: acids, bases or buffers to modify the ionic state, stability or dissolution properties of the resulting dispersion; fillers, binders, disintegrants or other materials to improve the tableting process or final properties of the tablet such as tablet hardness or friability and the dissolution of the dispersion; antioxidants to improve the dispersion's stability; osmotic agents, including both osmotically effective solutes such as sugars, salts and polyols as well as surfactants, all of which affect the wetting or dissolution rate of the dispersion itself, as well as the dissolution rate of any granules, beads, tablets or capsules into which the dispersion has been incorporated.

In particular, it is desirable to add excipients to the spray solution that will improve the manner in which the dispersion wets, disperses, disintegrates and ultimately dissolves when introduced into an aqueous use environment.

Since Drug A is itself hydrophobic and a number of the concentration-enhancing polymers suitable for forming dispersions show a tendency to agglomerate to form "hydrogel"-type materials in aqueous solutions, addition of hydrophilic materials that swell or dissolve readily in aqueous solution are desirable.

Suitable agents to accomplish this goal include (1) surfactants such as polyoxamers, sold under trade names such as PLURONIC, and polyoxyethylene sorbitan fatty acid esters, sold under the trade name TWEEN; (2) water-swellable or water-soluble polymers such as methylcellulose, hydroxyethylcellulose, hydroxypropylcellulose, hydroxypropyl methyl cellulose, crosslinked or uncrosslinked polyvinylpyrrolidone, polydextrose, starch glycolate and its salts and crosslinked or uncrosslinked carboxymethyl cellulose; and (3) hydrophilic solutes such as sugars (glucose, sucrose, lactose), carboxylic acids (citric acid, tartaric acid) or salts (sodium chloride, sodium acetate, sodium phosphate).

The amount of excipient to be added to the spray solution can vary widely depending on the type of excipient. For example, when a surfactant is added to the spray solution, often only a small amount is required to be added to positively affect the wetting properties of the dispersion, typically 0.1 to 5.0 wt % of the solids in the spray solution. For water-soluble polymers that promote disintegration of tablets or granules, typically the amount added makes up 1 to 10 wt % of the solids in the spray solution. In the case of hydrophilic solutes, larger amounts are often required, on the order of up to 50 wt % of the final dispersion.

As mentioned above, such excipients may be dissolved along with Drug A and one or more concentration-enhancing polymers in the spray solvent or may be suspended in the spray solution. To maximize distribution of the excipient throughout the dispersion it is often desirable to choose a solvent in which the excipient is soluble. For some hydrophilic excipients, this may require, for example, adding water or other solvent to the spray solution to enhance excipient solubility.

In some cases, however, it is preferred that the excipient is only suspended in the spray solution, inasmuch as a homogeneous mixture in the dispersion may adversely affect the physical or chemical stability of Drug A. For example, mixing a large amount of a polymer with a low $T_g$ value into the dispersion may decrease the physical stability of the dispersion by lowering the overall $T_g$ of the dispersion. Generally, it is preferred that the $T_g$ of the composition be greater than the storage temperature of the composition. Thus, preferably the $T_g$ of the composition is greater than about 40° C., more preferably greater than 60° C. When the excipient is suspended in the spray solution it is generally preferred that the excipient particle size be quite small, typically less than 100 μm and preferably less than 20 μm in average size.

Solvents suitable for spray-drying may be essentially any organic compound or mixtures of an organic compound and water in which Drug A and polymer are mutually soluble. Because Drug A has low water solubility, water alone is not a suitable solvent. However, mixtures of water and organic compounds are often suitable. Preferably, the solvent is also relatively volatile with a boiling point of 150° C. or less. However, in those cases where the solubility of Drug A in the volatile solvent is low, it may be desirable to include a small amount, say 2 to 25 wt %, of a low volatility solvent such as N-methylpyrrolidone (NMP), dimethylsulfoxide (DMSO) or dimethylacetamide (DMAc) in order to enhance Drug A's solubility in the solvent mixture. Preferred solvents include lower alcohols such as methanol, ethanol, n-propanol, isopropanol, and butanol; ketones such as acetone, methyl ethyl ketone and methyl isobutyl ketone; esters such as ethyl acetate and propylacetate; and various other solvents such as acetonitrile, methylene chloride, toluene, and 1,1,1-trichloroethane. Especially preferred are methanol, acetone, mixtures of methanol and water, mixtures of acetone with water, and mixtures of methanol and acetone with water. In particular, a mixture of acetone and water with a water content between about 2 and 10 wt % has been found to yield excellent results when the concentration-enhancing polymer is HPMCAS.

The various spray solutions described above can be spray-dried under a wide variety of conditions and yet still yield dispersions with acceptable properties. For example, various types of nozzles can be used to atomize the spray solution, thereby introducing the spray solution into the spray-dry chamber as a collection of fine droplets. Essentially any type of nozzle may be used to spray the solution as long as droplets are formed that are sufficiently small that they are sufficiently dry (due to evaporation of solvent) by the time they impinge on the wall of the spray-drying chamber that they do not stick to or coat the wall.

Although the maximum droplet size varies widely as a function of the size, shape and flow pattern within the spray-dryer, it is generally true that droplets should be less than about 500 μm in diameter when they exit the nozzle. In many cases, spray-drying conditions are chosen that require the droplets be less than about 20 to 50 μm in diameter. One specific type of spray-dryer that has been successfully used to make dispersions of the present invention is the Niro portable Model PSD-1. Three types of nozzles that have successfully been used in this spray-dryer are the "fountain" type (a NIRO #HDO-046E with a NIRO 2.25 mm orifice disc #15633-0225 or a SPRAY SYSTEMS 1/8JN-SS with liquid cap #60150 and air cap #180), the "flat fan" type (SPRAY SYSTEMS 1/8JN-SS with liquid cap #60150 and air cap #189-6-62-160) and the "two-fluid" type (NIRO 2-fluid nozzle, cocurrent, external mix, with a 1.0 mm liquid orifice #15698-0100). When using the "fountain type" nozzle, spray solution is sprayed upward from the bottom of the spray-drying chamber and drying gas is introduced into the top of the chamber. When using the "flat fan" type or the "two-fluid" type nozzles, the solution is sprayed from the center of the top of the spray-drying chamber and the drying gas is introduced through an annular channel at the top of the chamber that surrounds the nozzle. Multiple nozzles can also be used simultaneously.

The spray solution can be delivered to the spray nozzle or nozzles at a wide range of temperatures and flow rates. Generally, the spray solution temperature can range anywhere from just above the freezing point to about 20° C. above the ambient pressure boiling point of the solvent, i.e., by placing the solution under pressure and in some cases even higher. For solutions of Drug A and concentration-enhancing polymer in acetone or an acetone/water mixture, good results can be obtained by spraying a solution at a temperature ranging from about 0° to about 70° C. Typically, solutions are sprayed at a temperature of 10° to 40° C.

Spray solution flow rates to the spray nozzle can vary over a wide range depending on the type of nozzle, spray-dryer size and spray-dry conditions such as the inlet temperature and flow rate of the drying gas. Generally, the energy for evaporation of solvent from the spray solution in a spray-drying process comes primarily from the drying gas. The relationship between the temperature drop of the drying gas and the flow rate of the spray solution is generally linear, i.e., the greater the difference between the temperature of the drying gas from the point at which it enters the drying chamber ($T_{in}$) to the point at which it exits the drying chamber ($T_{out}$) or ($T_{in}$ minus $T_{out}$), the greater is the flow rate of the spray solution.

However, if the liquid spray flow rate is too high, the drying gas will cool to the point that the temperature drops significantly below the boiling point of the solvent. When this occurs, solvent evaporation slows to the point that the droplets are not sufficiently dry by the time they impinge on the drying chamber wall to form the desired powdered material. Thus, the liquid spray solution flow rate is preferably sufficiently low that $T_{out}$ is no more than about 30 to 50° C. less than the boiling point of the solvent. In addition, to prevent the dispersion components from being exposed to excessive temperatures and resulting discoloration or chemical degradation, the spray solution flow rate is preferably sufficiently high that $T_{out}$ is no more than about 150° C. or, when the boiling point of the solvent is 100° C. or less, no more than about 120° C.

The drying gas can, in principle, be essentially any gas, but for safety reasons and to minimize undesirable oxidation of Drug A or other materials in the dispersion, an inert gas such as nitrogen, nitrogen-enriched air or argon is utilized. The drying gas is typically introduced into the drying chamber at a temperature between about 60° and 300° C. and preferably between about 80° and 240° C. For example, when the spray solution is composed of 7.5 wt % Drug A, 7.5 wt % HPMCAS-MF, 80.75 wt % acetone and 4.25 wt % water, excellent results are obtained when the drying gas inlet temperature is about 100° to about 200° C. and the outlet temperature is between about 30° and 80° C.

The solid dispersion made via the spray-drying process described above comprises a fine powder with an average particle size ranging from about 2 to about 200 μm in diameter. The density of such a fine powder can range from about 0.02 to about 0.4 g/cm$^3$. The spray-dried dispersion is separated from the drying gas and collected by any convenient means such as a cyclone or a filter such as a porous screen filter or a bag filter.

Spray-drying may also be combined with other processes in order to form the solid dispersion of Drug A, such as with fluid bed drying and/or vacuum drying and/or wet granulation during or following spray-drying, spray-coating and freeze-drying. When the composition has been formed using a solvent process, the drug/polymer composition can be dried to remove residual solvent. Generally, it is desired that the drying process remove residual solvent in the composition to less than 1 wt %, preferably less than 0.1 wt %. Examples of suitable drying processes include tray drying, fluid bed drying, microwave drying, belt drying, rotary drying, and other drying processes known in the art. See, for example, *The Theory and Practice of Industrial Pharmacy* by Lachman, et al. (1986)

In tray drying, the dispersion containing Drug A is spread onto a shallow tray, typically at a depth of about 0.5 to 10 cm, preferably 1 to 4 cm. The tray is then placed into an oven held at a temperature ranging from 25 to 60° C., preferably 30 to 50° C. Air at the temperature of the oven is then circulated through the dryer to remove residual solvent. The drying process can last from 2 to 24 hours, more typically 4 to 16 hours.

In fluid bed drying the composition is added to a chamber and a fluidizing/drying gas is introduced at a rate sufficient to fluidize the composition particles. The temperature of the fluidizing/drying gas generally ranges from 25 to 60° C., preferably 30 to 50° C. A fluid bed drying process typically will last from 0.25 to 8 hours, more typically from 0.5 to 4 hours.

As described below, various types of immediate-, delayed-, controlled- or sustained-release dosage forms can be prepared comprising the above solid dispersions and various other excipients.

Drug Dispersion and Additional Concentration-Enhancing Polymer

A second aspect of the present invention is a pharmaceutical composition comprising any of the above amorphous solid dispersions of Drug A and an additional amount of concentration-enhancing polymer, of the same or a different type from that used to form the dispersion. The composition may be conventional, such as a mixture or blend of the two components or the two components incorporataed into a dosage form. The composition of the two components may also be combined in situ, with an amorphous solid dispersion of Drug A and the polymer coming together in the environment of use. The amount of additional concentration-enhancing polymer added to the dispersion may vary widely, from near 0 to 20-fold the mass of Drug A.

A blend or mixture of the two components may be formed in any conventional way, including physical mixing by planetary mixers, vortex blenders, milling, extrusion, trituration, granulation, melt congealing or spray-drying. Such blends or mixtures may be incorporated into any of the dosage forms mentioned herein, and may include any of the additives, excipients or coatings mentioned herein.

The additional concentration-enhancing polymer can also be incorporated as a coating to the dispersion particles, with or without additional excipients, via wet granulation processes such as fluidized bed granulation or by coating in a fluid-bed coating process by coating individual dispersion particles or by coating preformed granules, beads, tablets, or capsules (in which case the polymer may form, e.g., the capsule wall).

The pharmaceutical composition of amorphous solid dispersion of Drug A and additional concentration-enhancing polymer may be effectively achieved in situ by coadministration of (1) any of the compositions of amorphous solid dispersions of Drug A mentioned above, and (2) additional concentration-enhancing polymer. By "coadministration" is meant delivery of (1) and (2) to an environment of use at substantially the same time or sufficiently close in time to achieve the improvements in bioavailability of Drug A mentioned herein, generally not greater than 60 minutes, preferably not greater than 15 minutes apart. In connection with such co-administration, either or both components may be separately incorporated into a dosage form so as to facilitate the formation of the pharmaceutical composition in situ. For example, if the amorphous solid dispersion of Drug A is incorporated into a dosage form, certain cellulosic polymers such as HPMCAS are formable in tablet or capsule form, making co-administration of the two components readily achievable.

Amorphous Drug and Concentration-Enhancing Polymer

A third basic form of the pharmaceutical composition of the present invention comprises amorphous Drug A and concentration-enhancing polymer. Just as noted above in connection with the second aspect of the invention, the composition may be conventional, such as a blend or a mixture or in a dosage form, or may be effectively formed in the environment of use, i.e., in situ, with ones or both, of the two components incorporated into a dosage form prior to co-administration. The concentration-enhancing polymer may also be incorporated as a coating in any of the ways mentioned in connection with the second aspect of the invention.

Amorphous forms of Drug A include both (1) substantially amorphous materials composed of Drug A alone; and (2) substantially amorphous materials composed of Drug A and one or more excipients other than concentration-enhancing polymer. This second type of amorphous form of Drug A can, for example, be a solid amorphous dispersion of Drug A in a material other than the concentration-enhancing polymer.

When the amorphous form of Drug A is composed of Drug A alone, it may be prepared by any known method for rendering materials amorphous that are crystalline in their lowest energy, equilibrium state. Such methods include (1) solvent processing, where Drug A is dissolved in a solvent and then solidified by removal of solvent by evaporation or precipitation in a non-solvent; (2) thermal processing, wherein Drug A is melted and then cooled; (3) mechanical processing, wherein Drug A is rendered amorphous by mechanical energy; and (4) combinations of (1) to (3).

Any of the processes previously listed as appropriate for forming dispersions may be used to form amorphous Drug A. In particular, amorphous Drug A may be made by dissolving in a solvent such as acetone or methanol and spray-drying in generally the same manner in which is described above for making dispersions of Drug A in concentration-enhancing polymer. Amorphous Drug A may also be made, for example, by feeding crystalline Drug A to a melt congeal apparatus such as that disclosed in U.S. Pat. Nos. 5,183,493 or 5,549,917 such that droplets of molten Drug A are formed and then cooled by a cooling gas to form amorphous particles of Drug A ranging from about 1 to about 500 μm in diameter and preferably about 10 to 300 μm in diameter.

Amorphous Drug A alone (with no excipients) can be characterized by thermal analysis via DSC. When a sample of dry amorphous Drug A alone is subjected to DSC analysis at a scan rate of about 10° C. per minute, the sample generally shows a glass transition temperature ($T_g$) of about 90° to 100° C. and an exothermic peak due to the crystallization of Drug A of about 170° to 190° C. At even higher temperatures the DSC scan shows crystallized Drug A melting (an endotherm) at about 238° C. When amorphous Drug A alone is exposed to humidity it absorbs water, leading to a decrease in the observed $T_g$ and crystallization temperatures. For example, amorphous state Drug A alone equilibrated with 25% relative humidity at about 20 to 25° C. shows a $T_g$ of about 60° to 90° C. and a crystallization exotherm at about 160° to 180° C. The relative high values of the $T_g$ and crystallization temperatures for amorphous state Drug A are an indication that the amorphous state is particularly stable, allowing Drug A to be formulated as the amorphous state.

The amorphous nature of Drug A can also be verified by Powder X-ray Diffraction (PXRD) analysis which generally should show diffuse scattering bands rather than sharp scattering lines due to the presence of crystalline Drug A. Generally, a major portion of Drug A is amorphous, meaning that at least 60% of Drug A is in the amorphous form. Preferably, amorphous Drug A should be substantially all in the amorphous state, meaning that 25 wt % or less of Drug A is in a crystalline state and preferably essentially all of Drug A is in the amorphous state, meaning that less than 10 wt % of Drug A is in a crystalline state, all as evidenced by DSC or PXRD analysis.

Alternatively, amorphous state Drug A may be a substantially amorphous material composed of Drug A and one or more excipients other than a concentration-enhancing polymer. For example, to promote the physical or chemical stability of amorphous state Drug A or to facilitate the incorporation of amorphous state Drug A into the various types of dosage forms disclosed herein, a dispersion of Drug A in one or more excipients may be formed in much the same manner that dispersions of Drug A in a concentration-enhancing polymer are formed, as described above.

For example, a dispersion of Drug A in a matrix comprising any of a wide variety of material such as citric acid, a sugar such as sucrose, lactose, or polydextrose, a lipid or a wax such as a fatty acid ester of glycerol, may be made by subjecting a solid or molten feed to a melt congeal process as described above for making amorphous Drug A alone. The resulting material may be a solid solution of Drug A in the dispersion matrix material or Drug A and the excipients may separate into different phases as long as Drug A is substantially in the amorphous state.

Exemplary melt congeal processes and excipients are described in U.S. Pat. No. 5,183,493, the disclosure of which is incorporated herein by reference; this patent describes the formation of beads by coagulation of molten droplets from a liquid feed. Another suitable melt congeal or "flash flow" process applies heat or a shear force or both to a solid feed so as to temporarily liquify part or all of the feed. See U.S. Pat. Nos. 5,849,223, 5,549,917, 5,236,734 and 5,238,696, the disclosures of all of which are incorporated herein by reference.

Although in some cases such melt congeal processes can be operated so that primarily the excipients melt so as to entrap or coat crystalline Drug A by the excipients, in the context of this invention, such processes should be conducted so that Drug A present in the resulting particulates is substantially amorphous. This condition implies that the mixture of Drug A and excipients reach, at least temporarily, a condition of temperature and shear such that crystalline Drug A melts or dissolves in the molten excipients. Appropriate excipients to use in such processes generally include any pharmaceutically approved material that has a melting point between about 40° C. and 250° C. Exemplary excipients include fats such as the hydrogenated or partially hydrogenated versions of vegetable oils such as cotton seed, palm, or soybean oils; mono-, di-, and tri-glycerides of fatty acids; propylene glycol or ethylene glycol mono- and di-esters of fats and fatty acids; waxes; and long chain alcohols. It should also be noted that other excipients may be added to the melt congeal-processed mixture that may improve processing, stability or dissolution, such as surfactants, emulsifiers, solvents or aqueous-soluble polymers.

The amorphous state Drug A material is then combined with a sufficient amount of concentration-enhancing polymer to meet one or more of the in vitro or in vivo performance requirements to form the compositions of the invention. Generally, the amount of concentration-enhancing polymer combined with amorphous state Drug A is from about half up to about 20-fold the mass of Drug A. Amorphous state Drug A and the concentration-enhancing polymer may be combined in any way that achieves at least one of the following objectives: (1) Drug A and the concentration-enhancing polymer are both dissolved in an aqueous environment of use (such as an in vitro test media or the fluids in the GI tract of a mammal) sufficiently to meet the solubility criteria of the present invention; or (2) a relative bioavailability of Drug A is achieved that is at least 1.25 compared to a control of amorphous Drug A alone (i.e., in the absence of concentration-enhancing polymer).

Compositions can be simple physical mixtures of amorphous state Drug A and one or more concentration-enhancing polymers, or can be formed in a granulation process, or the concentration-enhancing polymer can be applied from a solution as a coating to a powder, to granules, to capsules or to tablets containing the amorphous state Drug A.

For example, blends may be formed in any conventional way such as by blending the dry ingredients including the amorphous state Drug A, one or more concentration-enhancing polymers, and any other excipients appropriate to forming the desired dosage form using V-blenders, planetary mixers, vortex blenders, mills, extruders such as twin-screen extruders and trituration processes. The ingredients can be combined in granulation processes utilizing mechanical energy, such as ball mills or roller compactors. They may also be combined using wet granulation methods in high-shear granulators or fluid bed granulators wherein a solvent or wetting agent is added to the ingredients or the concentration-enhancing polymer may be dissolved in a solvent and used as a granulating fluid. The concentration-enhancing polymer may be added as a coating to tablets preformed by a compression process from a mixture containing the amorphous state Drug A, the coating taking place in a spray-coating process using, for example, a pan coater or a fluidized-bed coater.

Post-Fabrication Processing

Once any of the foregoing drug/polymer compositions has been formed, several processing operations can be used to facilitate incorporation of the composition into a dosage form. These processing operations include drying, granulation, and milling.

The drug/polymer composition may be granulated to increase particle size and improve handling of the composition while forming a suitable dosage form. Preferably, the average size of the granules will range from 50 to 1000 µm. Such granulation processes may be performed before or after the composition is dried, as described above. Dry or wet granulation processes can be used for this purpose. An example of a dry granulation process is roller compaction. Wet granulation processes can include so-called low shear and high shear granulation, as well as fluid bed granulation.

When the drug/polymer composition is made using a mixing or blending process, the granulation process can occur in the same equipment used to form the blend. High shear or high speed mixers/granulators are routinely used for processing pharmaceutical compositions. In these processes, a granulation fluid is mixed with the composition after the dry components have been blended to aid in the formation of the granulated composition. Examples of granulation fluids include water, ethanol, isopropyl alcohol, n-propanol, the various isomers of butanol, and mixtures thereof.

If a wet granulation process is used, the granulated composition is often dried prior to further processing. Examples of suitable drying processes to be used in connection with wet granulation are the same as those described above. Where the drug/polymer composition is made by a solvent process, the composition can be granulated prior to removal of residual solvent. During the drying process, residual solvent and granulation fluid are concurrently removed from the composition.

Once the composition has been granulated, it may then be milled to achieve the particle size required for the specific dosage form. Examples of suitable processes for milling the composition include hammer milling, ball milling, fluid-energy milling, roller milling, cutting milling, and other milling processes known in the art.

When the drug/polymer composition is made by a spray-drying process, the spray-drying and fluid bed drying processes can be performed in the same piece of equipment. Here, the spray-dried particles formed in the spray-drying chamber can be directed to a second chamber where a fluidizing/drying gas is added to fluidize the particles and remove residual solvent. Alternatively, the particles from the spray-drying chamber can be continuously fed to a continuous dryer, such as a belt dryer or rotary drum dryer. Such "hybrid" systems have the advantage of allowing the spray-drying process to be optimized for its concentration-enhancing properties, as well as for density and particle size, rather than merely for solvent removal, with solvent removal taking place in the fluid bed drying chamber or the continuous drying process.

In other embodiments when the drug/polymer composition is made by a spray-drying process, the spray-dried particles formed in the spray-drying chamber can be directed to a second chamber where a wet, fluidized bed granulation process can be performed. Here, a granulation fluid is sprayed into the granulation chamber to increase the density and particle size of the spray-dried dispersion. This process also has the advantage of allowing the spray-drying process to be optimized for its concentration-enhancement properties as well as for residual solvent removal and therefore for stability of the dispersion. The granulation process can then be used to obtain a composition with the desired density and particle size.

In yet another embodiment when the drug/polymer composition is made by a spray-drying process, the spray-dryer can be equipped with both a granulation chamber and a fluid bed drying chamber, such that formation of the spray-dried dispersion, granulation, and drying can all be achieved in a single apparatus.

Alternatively, granulation can be achieved within the spray-drying chamber by spraying a second granulating fluid into the chamber simultaneously with the spray-drying process.

Incorporation Into Immediate Release Dosage Forms

The three basic types of pharmaceutical compositions of the invention may be used to formulate any conventional known dosage form. In general, many conventional materials and procedures for formulation and preparation of oral dosage forms of drugs may be used by simply substituting the compositions of this invention for the drug or active agent that is to be dispensed from the known dosage form.

Thus, (1) solid amorphous dispersions of Drug A in one or more concentration-enhancing polymers; (2) the dispersion of (1) plus additional concentration-enhancing polymer; and (3) compositions of an amorphous state form of Drug A and one or more concentration-enhancing polymers may all be formulated into a wide range of immediate release dosage forms, including the following: (A) tablets, (B) multiparticulates, (C) oral suspensions, and (D) capsules. In some cases, formulations may constitute a combination of such dosage forms. For example, one or more types of multiparticulates or a suspension may be formed and then incorporated into a capsule or simply be packaged as an OPC or a sachet, as explained below.

(A) Tablets

Tablets are generally formed by blending the compositions of this invention with appropriate excipients and then compressing the powder to form tablets using any of a wide variety of presses used in the fabrication of pharmaceutical dosage forms. Often it is desirable to granulate the compositions themselves, with or without the addition of excipients prior to compression. For example, the dispersions or mixtures that constitute the compositions of this invention may be granulated by mechanical means by, for example, roller compaction or "slugging," followed by milling to form granules. The granules typically have improved flow, handling, blending and compression properties relative to the ungranulated materials. In addition, improved wetting, disintegrating, dispersing and dissolution properties may be obtained by the inclusion of excipients in addition to the compositions themselves.

Alternatively, when the compositions consist of two separate materials, such as amorphous state Drug A and one or more concentration-enhancing polymers, one component, such as the amorphous state Drug A, may be granulated alone or as a blend with the appropriate excipients, and the second component, in this case at least one concentration-enhancing polymer, may be added in a variety of ways including: (1) dissolving or suspending in the granulating solvent followed by any known wet granulating process such as high-shear granulation or fluid-bed granulation; (2) mixing with the amorphous state Drug A containing granules prior to compression; (3) dissolving or suspending the concentration-enhancing polymer(s) in a solvent and coating the granules prior to compression; and (4) first forming a tablet by compression of the amorphous state Drug A and other excipients, with or without granulation, followed by coating the tablets with concentration-enhancing polymer(s) using a solution or suspension of the polymer(s) in a solvent.

Excipients that may be included in the immediate-release dosage forms include any of those known in the pharmaceutical arts and include surfactants, pH modifiers, matrix materials, complexing agents, solubilizers, fillers, disintegrating agents (disintegrants), binders, or lubricants.

One very useful class of excipients is surfactants, preferably present from 0 to 10 wt %. Suitable surfactants include fatty acid and alkyl sulfonates; commercial surfactants such as benzalkonium chloride (HYAMINE® 1622, available from Lonza, Inc., Fairlawn, N.J.); dioctyl sodium sulfosuccinate (DOCUSATE SODIUM, available from Mallinckrodt Spec. Chem., St. Louis, Mo.); polyoxyethylene sorbitan fatty acid esters (TWEEN®, available from ICI Americas Inc., Wilmington, Del.; LIPOSORB® o-20, available from Lipochem Inc., Patterson N.J.; CAPMUL® POE-0, available from Abitec Corp., Janesville, Wis.); and natural surfactants such as sodium taurocholic acid, 1-palmitoyl-2-oleoyl-sn-glycero-3-phosphocholine, lecithin, and other phospholipids and mono- and diglycerides. Such materials can advantageously be employed to increase the rate of dissolution by, for example, facilitating wetting, or otherwise increase the $c_{max}$ attained.

Addition of pH modifiers such as acids, bases, or buffers may also be beneficial in an amount of from 0 to 10 wt %. Such pH modifiers retard the dissolution of the pharmaceutical composition (e.g., acids such as citric acid or succinic acid when the dispersion polymer is anionic) or, alternatively, enhance the rate of dissolution of the pharmaceutical composition (e.g., bases such as sodium acetate or amines). In the case of dispersions of Drug A, addition of conventional matrix materials, surfactants, fillers, disintegrants, or binders may be added as part of the dispersion itself, added by granulation via wet or mechanical or other means. When such additives are included as part of the dispersion itself, they may be mixed with drug and polymer(s) in the spray-drying solvent, and may or may not dissolve along with the drug and polymer(s) prior to forming the dispersion by spray-drying.

Other conventional formulation excipients may be employed in the compositions of this invention, including those excipients well-known in the art (e.g., as described in *Remington's Pharmaceutical Sciences* (16th ed. 1980). Generally, excipients such as fillers, disintegrating agents, pigments, binders, lubricants, glidants, flavorants, and so forth may be used for customary purposes and in typical amounts without adversely affecting the properties of the compositions. These excipients may be utilized after the drug/polymer composition has been formed, in order to formulate the composition into tablets, capsules, suspensions, powders for suspension, creams, transdermal patches, and the like.

Examples of other matrix materials, fillers, or diluents include lactose, mannitol, xylitol, dextrose, sucrose, sorbitol, compressible sugar, microcrystalline cellulose, powdered cellulose, starch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers such as polyethylene oxide, and hydroxypropyl methyl cellulose.

Examples of surface active agents include sodium lauryl sulfate and polysorbate 80.

Examples of drug complexing agents or solubilizers include the polyethylene glycols, caffeine, xanthene, gentisic acid and cylodextrins.

Examples of disintegrants include sodium starch glycolate, sodium carboxymethyl cellulose, calcium carboxymethyl cellulose, croscarmellose sodium, crospovidone (polyvinylpolypyrrolidone), methyl cellulose, microcrystalline cellulose, powdered cellulose, starch, pregelatinized starch, and sodium alginate.

Examples of tablet binders include acacia, alginic acid, carbomer, carboxymethyl cellulose sodium, dextrin, ethylcellulose, gelatin, guar gum, hydrogenatetd vegetable oil, hydroxyethyl cellulose, hydroxypropyl cellulose, hydroxypropyl methyl cellulose, methyl cellulose, liquid glucose, maltodextrin, polymethacrylates, povidone, pregelatinized starch, sodium alginate, starch, sucrose, tragacanth, and zein.

Examples of lubricants include calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate.

Examples of glidants include silicon dioxide, talc and cornstarch.

The following are exemplary methods for forming immediate release tablets of the present invention for compositions consisting of amorphous solid dispersions of from 10 to 60 wt % Drug A in a concentration-enhancing polymer such as HPMCAS, formed by a spray-drying process. In one method, the solid dispersion alone is first granulated by roller compacting at a roller pressure of about 30 Kgf/cm$^2$ and then the resulting "ribbon" is ground in a Comill mill. A mean particle size of 130 μm is obtained using a power setting of about 2 to 6 and a screen size of 032R to 055R. The resulting material is then blended with microcrystalline cellulose, croscarmellose sodium and magnesium stearate. The amounts of each ingredient may vary depending on the amount of Drug A desired in the final tablet. However, generally the solid dispersion should comprise about 10 to about 70 wt % of the blend, magnesium stearate about 0.2 to about 2.0 wt %, croscarmellose sodium about 1.0 to about 20.0 wt %, with microcrystalline cellulose making up the balance of the blend. The blends are then compressed into tablets weighing from about 200 to 800 mg on a tablet press such as a Kilian T-100. Compression force is generally adjusted to achieve a tablet hardness of about 5 to 20 kP.

Alternatively, the excipients and dispersion may first be blended in, for example, a V-blender followed by the formation of granules by roller compaction of the blend followed by milling to a mean granule size of about 100 μm to 300 μm. It is often desirable to add only the minimum amount of lubricant (magnesium stearate) to the blend prior to roller compaction so as to prevent the blend from sticking to the rollers, typically only 0.1 to 0.4 wt %. The remaining lubricant is blended with the granulated material just prior to tableting.

In another method, about 10 to 77 wt % of the solid dispersion (containing 10 to 60 wt % Drug A in a concentration-enhancing polymer such as HPMCAS or CAP), about 5 to about 40 wt % of dibasic calcium phosphate, about 5 to about 40 wt % of microcrystalline cellulose, and about 5 to about 25 wt % of crospovidone may first be blended in, for example, a V-blender, followed by de-lumping through a screen and then addition of about 0.2 to about 2 wt % of a lubricant such as magnesium stearate and further blending. The blend may then be densified using a roller compactor. The size of the compacts may then be reduced by milling to form granules with a mean granule size of about 100 μm to 300 μm. An additional portion of lubricant may then be added to the granules and the mixture blended prior to tableting. A film coating may also be applied to these tablets using conventional pan-coating techniques.

Of course, other choices of excipients and processes as are known in the pharmaceutical arts and are described briefly above may be substituted for the exemplary tablets and process described above.

(B) Multiparticulates

Multiparticulates generally refer to dosage forms that comprise a multiplicity of particles that may range in size from about 10 μm to about 2 mm, more typically about 100 μm to 1 mm in diameter. Such multiparticulates may be packaged, for example, in a capsule such as a soft gelatin capsule or a capsule formed from an aqueous-soluble polymer such as HPMC, HPMCAS or starch or they may be dosed as a suspension or slurry in a liquid or combined with food. Such particulates may be made by any known process such as wet and dry granulation processes or melt congeal processes such as those previously described for forming amorphous state Drug A. For example, Drug A and a glyceride such as hydrogenated vegetable oil, a vegetable or synthetic fat or a wax such a paraffin may be blended and fed to a melt congeal process as a solid or liquid, followed by cooling to form beads comprised of amorphous Drug A and the excipient.

The so-formed beads may then be blended with one or more concentration-enhancing polymers with or without additional excipients to form a multiparticulate dosage form.

Alternatively, a high melting point concentration-enhancing polymer such as HPMCAS may be blended with Drug A and the fat or wax fed as a solid blend to a melt congeal process or the blend may be heated such that Drug A and the fat or wax melt to form a slurry of concentration-enhancing polymer particles in molten Drug A and fat or wax. The resulting material comprises beads or particles consisting of an amorphous dispersion of Drug A in the fat or wax with concentration-enhancing polymer particles trapped therein. Alternatively, a dispersion of Drug A in a concentration-enhancing polymer may be blended with a fat or wax and then fed to a melt congeal process as a solid or a slurry of the dispersion in the molten fat or wax. Such processing yields particles or beads consisting of particles of dispersion trapped in the solidified fat or wax matrix.

Similar multiparticulate dosage forms may be made with the various compositions of this invention but using excipients suited to the bead-forming or granule-forming process chosen. For example, when granules are formed by extrusion/spheronization processes the dispersion or other composition may be blended with, for example, microcrystalline cellulose or other cellulosic polymer to aid in processing.

In any case, the resulting particles may themselves constitute the multiparticulate dosage form or they may be coated by various film-forming materials such as enteric polymers or water-swellable or water-soluble polymers, or they may be combined with other excipients or vehicles to aid in dosing to patients.

(C) Oral Suspensions

The compositions of the present invention may be formulated in various forms such that they are delivered as a suspension of particles in a liquid vehicle. Such suspensions may be formulated as a liquid or paste at the time of manufacture, or they may be formulated as a dry powder with a liquid, typically water, added at a later time but prior to oral administration. Such powders that are constituted into a suspension are often termed sachets or oral powder for constitution (OPC) formulations. Such dosage forms can be formulated and reconstituted via any known procedure. The simplest approach is to formulate the dosage form as a dry powder that is reconstituted by simply adding water and agitating. Alternatively, the dosage form may be formulated as a liquid and a dry powder that are combined and agitated to form the oral suspension. In yet another embodiment, the dosage form can be formulated as two powders which are reconstituted by first adding water to one powder to form a solution to which the second powder is combined with agitation to form the suspension.

Generally, it is preferred that the dispersion of Drug A or amorphous form of Drug A be formulated for long-term storage in the dry state as this promotes the chemical and physical stability of Drug A. Various excipients and additives are combined with the compositions of the present invention to form the dosage form. For example, it may be desirable to add some or all of the following: preservatives such as sulfites (an antioxidant), benzalkonium chloride, methyl paraben, propyl paraben, benzyl alcohol or sodium benzoate; suspending agents or thickeners such as xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, or titanium dioxide; anticaking agents or fillers such as silicon oxide, or lactose; flavorants such as natural or artificial flavors; sweeteners such as sugars such as sucrose, lactose, or sorbitol as well as artificial sweeteners such as aspartame or saccharin; wetting agents or surfactants such as various grades of polysorbate, docusate sodium, or sodium lauryl sulfate; solubilizers such as ethanol propylene glycol or polyethylene glycol; coloring agents such as FD and C Red No. 3 or FD and C Blue No. 1; and pH modifiers or buffers such as carboxylic acids (including citric acid, ascorbic acid, lactic acid, and succinic acid), various salts of carboxylic acids, amino acids such as glycine or alanine, various phosphate, sulfate and carbonate salts such as trisodium phosphate, sodium bicarbonate or potassium bisulfate, and bases such as amino glucose or triethanol amine.

A preferred additive to such formulations is additional concentration enhancing polymer which may act as a thickener or suspending agent as well as to enhance the concentration of Drug A in the environment of use and may also act to prevent or retard precipitation or crystallization of Drug A from solution. Such preferred additives are hydroxyethyl cellulose, hydroxypropyl cellulose, and hydroxypropyl methyl cellulose. In particular, the salts of carboxylic acid functional polymers such as cellulose acetate phthalate, hydroxypropyl methyl cellulose acetate succinate, and carboxymethyl cellulose are useful in this regard. Such polymers may be added in their salt forms or the salt form may be formed in situ during reconstitution by adding a base such as trisodium phosphate and the acid form of such polymers.

Exemplary oral powders for constitution can be prepared by combining the compositions of the present invention with a surfactant, a solubilizer, and a suspending agent by dry blending. For example, 1.2 g of a solid amorphous dispersion comprising, for example, 25 wt % Drug A and 75 wt % HPMCAS-MF, is combined with 0.15 g polyoxyethylene 20 sorbitan monooleate (solid under the name Tween 80), and 2.70 g polyethylene glycol 3350. The solid mixture is constituted as a suspension by addition of 27.15 g of water followed by agitation. Alternatively, an aqueous solution of 0.5 wt % TWEEN 80 and 9.0% polyethylene glycol 3350 can first be formed and then 30 ml of the solution added to 1.2 g of solid amorphous dispersion comprising, for example, 25 wt % Drug A and 75 wt % HPMCAS-MF, in a vial. The capped vial is then shaken vigorously to form the suspension and then dosed orally to a mammal. In some cases it may be desirable to add from 0.2 to 2.0 g of additional concentration enhancing polymer such as HPMCAS-MF or HPMC or CAP to the formulation to further enhance the concentration of Drug A in the environment of use and, in turn, the bioavailability of Drug A. In some cases, it also may be desirable to add an acid or base to the formulation to retard or enhance dissolution of the concentration-enhancing polymer. In addition, it is often desirable to add up to 10 wt % of sucrose or sorbitol as a sweetener or, alternatively, an appropriate amount of an artificial sweetener such as aspartame, as well as a flavoring agent.

Although such oral suspension formulations are generally immediate release in nature, the release of Drug A can be delayed or sustained by modification of the formulation by, for example, processing the above ingredients to form granules that slowly dissolve or erode in the environment of use. For example, by increasing the level of enteric polymer such as HPMCAS, HPMCP, CAP, or CAT in the granules, the release of Drug A may be delayed for from 15 minutes up to several hours. Addition of water insoluble polymers or fats, waxes, oils or other compounds to the granules may further slow the dissolution of Drug A thereby obtaining a sustained release dosage form.

Such granules can be obtained by any known method such as those previously mentioned such as low-shear granulation, high-shear granulation, fluidized-bed granulation, melt-congeal processing, and roller compaction followed by milling. The delay- or sustained-release ingredients may be blended throughout the granules or added as a coating.

(D) Capsules

The compositions of the present invention may be delivered in the form of capsules filled with a fluid suspension or a dry powder. The powder may be a simple physical mixture of the composition, and appropriate excipients or all or a portion of the ingredients may be formed into granules or beads by any of the aforementioned granule-forming processes. The mixed ingredients are generally filled by conventional methods into two-part capsules formed from any pharmaceutically acceptable aqueous-soluble or erodible polymer. Exemplary materials for forming such capsule walls are gelatin, starch, methyl cellulose, poly vinyl alcohol, denatured gelatins, HPMC and HPMCAS. Minor amount of materials such as plasticizers, preservatives, opaquing agents, and dyes may be added as well.

Powders or granules are filled into one piece of the two-piece capsules (the body), and then the second piece, the cap, is put in place to seal the powder or granules in the capsule. Ingredients similar to those described above are often used in capsules except that thickeners or suspending agent are usually unnecessary and glidants or lubricants are often added to aid in filling and to prevent agglomeration of the capsule contents. Exemplary glidants or lubricants are glycol esters, silicones, silicon dioxide, stearic acid, stearic acid salts (e.g., magnesium stearate), and talc.

Controlled Release Dosage Forms

The compositions of the present invention may be used in many types of controlled release dosage forms, including those that provide delayed-release and sustained release of the composition. In one embodiment, the controlled release dosage form is one of the immediate release dosage forms described above, but coated with a suitable coating that controls the release of the composition from the dosage form. In another embodiment, dosage forms must be specifically formulated for controlled release of the composition. These controlled release dosage forms are described below.

Delayed Release Dosage Forms

The dosage compositions of the present invention may also be overcoated with one or more pH-sensitive coating compositions, commonly referred to in the art as "enteric" and "quasi-enteric" coatings, according to conventional procedures in order to delay the release of drug. Suitable pH-sensitive polymers include those which are relatively insoluble and impermeable at the pH of the stomach, but which are more soluble or disintegrable or permeable at the pH of the small intestine and colon. Such pH-sensitive polymers include polyacrylamides, phthalate derivatives such as acid phthalate of carbohydrates, amylose acetate phthalate, cellulose acetate phthalate (CAP), other cellulose ester phthalates, cellulose ether phthalates, hydroxypropylcellulose phthalate (HPCP), hydroxypropylethylcellulose phthalate (HPECP), hydroxyproplymethylcellulose phthalate (HPMCP), HPMCAS, methylcellulose phthalate (MCP), polyvinyl acetate phthalate (PVAcP), polyvinyl acetate hydrogen phthalate, sodium CAP, starch acid phthalate, cellulose acetate trimellitate (CAT), styrene-maleic acid dibutyl phthalate copolymer, styrene-maleic acid/polyvinylacetate phthalate copolymer, styrene and maleic acid copolymers, polyacrylic acid derivatives such as acrylic acid and acrylic ester copolymers, polymethacrylic acid and esters thereof, polyacrylic and methacrylic acid copolymers, shellac, and vinyl acetate and crotonic acid copolymers.

Preferred pH-sensitive polymers include shellac; phthalate derivatives; CAT; polyacrylic acid derivatives, particularly copolymers comprising acrylic acid and at least one acrylic acid ester; polymethyl methacrylate blended with acrylic acid and acrylic ester copolymers; and vinyl acetate and crotonic acid copolymers.

A particularly preferred group of pH-sensitive polymers includes CAP, PVAcP, HPMCP, HPMCAS, anionic acrylic copolymers of methacrylic acid and methylmethacrylate, and osmopolymers comprising acrylic acid and at least one acrylic acid ester.

It should be noted that many of the pH-sensitive polymers are also concentration-enhancing polymers, and so may be used to both enhance bioavailability and delay the release of Drug A.

To apply the pH-sensitive coating to the compositions of the present invention, the pH-sensitive polymer is first dissolved in a suitable solvent to form a coating solution. Useful solvents for this purpose include ketones, such as acetone; alcohols, such as methanol, ethanol, isopropyl alcohol, n-propyl alcohol, and the various isomers of butanol; chlorinated hydrocarbons, such as methylene chloride; water; and mixtures of these solvents. The polymer may also be suspended in the solvent.

The coating solution may also contain one or more plasticizers, such as polyethylene glycols, triethyl citrate, propylene glycols, diethyl phthalate, dibutyl phthalate, castor oil, triacetin, and others known in the art. The coating solution may also contain one or more emulsifiers, such as polysorbate-80.

Coating is conducted in conventional fashion, typically by dipping, spray-coating, or pan-coating. When coating tablets or capsules containing the composition of the present invention, the coating is preferably applied using a pan coater. When coating multiparticulates containing the compositions of the present invention, the coating is preferably applied using a fluidized-bed coater. The compositions of the present invention may also be coated by first granulating the composition using the methods described above, and then coating the granules in a fluidized-bed coater. The coated granules may then be incorporated into the dosage forms described above for immediate release.

In addition to the pH-sensitive polymers listed above, delayed release coatings may consist of a mixture or blend of two or more pH-sensitive polymers or may consist of a mixture of one or more pH-sensitive polymers and one or more non-pH-sensitive polymers. Addition of a non-pH-sensitive polymer to the pH-sensitive polymer is useful in modulating the duration of the delay or rate of release of drug from the granule, bead or tablet. For example, the delay can be lengthened by blending an aqueous-insoluble polymer with the pH-sensitive polymers, while the delay can be shortened by blending a water-soluble polymer with the pH-sensitive polymers. Preferred non-pH-sensitive aqueous-insoluble polymers include cellulose esters, cellulose ethers, polyacrylates, polyamides, polyesters, and vinyl polymers. Preferred non-pH-sensitive aqueous-soluble polymers include hydroxyalkyl-substituted cellulosics such as HPC, HEC and HPMC, PVA, PEG, PEO, PEG/PPG copolymers, and aqueous-soluble polyamides, polysaccharides, and polyacrylates. Various additives may be included in such coatings, including emulsifiers, plasticizers, surfactants, fillers and buffers.

Incorporation Into Erodible Matrix

The pharmaceutical compositions of Drug A may be formed into a dosage form specifically designed to provide controlled release of Drug A by an erosion or diffusion mechanism, the composition in turn being incorporated into an erodible polymeric matrix. By an "erodible" matrix is meant water-erodible or water-swellable or water-soluble in the sense of being either erodible or swellable or dissolvable in an aqueous environment or requiring the presence of an acid or base to ionize the polymeric matrix sufficiently to cause erosion or dissolution. The form of the device may be any known conventional form, including a tablet, a capsule, a caplet, a bead, a multiparticulate, a powder or combinations thereof, all as set forth in greater detail in commonly assigned and copending application Ser. No. 09/495,059, filed Jan. 31, 2000 and claiming the priority of Provisional Application Ser. No. 60/119,400 filed Feb. 10, 1999, the pertinent disclosure of which is incorporated herein by reference.

The drug may be delivered either in the form of a gel or a suspension of solids in water or primarily as a solution of Drug A, to the extent dissolution has taken place prior to erosion. While not wishing to be bound by any particular theory of delivery mechanism, the delivery is believed to take place by any one or more of the following mechanisms: (1) dissolution of the Drug A composition in the dosage form prior to erosion, coupled with diffusion from the dosage form, either directly or through a coating; (2) dissolution of the Drug A composition as the matrix erodes, with delivery primarily as a solution; or (3) delivery as a solid suspension as the matrix erodes, followed by dissolution in the GI tract.

Both the Drug A composition of the present invention and the erodible matrix component may contain osmagens, osmopolymers, solubility-enhancing agents and excipients. In addition, delayed or sustained release features may be added by coating the dosage form with controlled release coating formulations known in the art.

The erodible polymeric matrix into which the composition is incorporated may generally be described as a set of excipients that are mixed with the composition following its formation that, when contacted with the aqueous environment of use imbibes water and forms a water-swollen gel or "matrix" that entraps the composition. The water-swollen matrix gradually erodes, swells, disintegrates or dissolves in the environment of use, thereby controlling the release of drug to the environment of use. A key ingredient of this water-swollen matrix is the water-swellable, erodible, or soluble polymer which may generally be described as an osmopolymer, a hydrogel or a water-swellable polymer. Such polymers may be linear, branched, or crosslinked. They may be homopolymers or copolymers. They may be synthetic polymers derived from vinyl, acrylate, methacrylate, urethane, ester and oxide monomers.

Such materials include naturally occurring polysaccharides such as chitin, chitosan, dextran and pullulan; agar; gum agar, gum arabic, gum karaya, locust bean gum, gum tragacanth, carrageenans, gum ghatti, guar gum, xanthan gum and scleroglucan; starches such as dextrin and maltodextrin; hydrophilic colloids such as pectin; phosphatides such as lecithin; alginates such as ammonia alginate, sodium, potassium or calcium alginate, propylene glycol alginate; gelatin; collagen; and cellulosics.

A preferred class of cellulosics for the erodible matrix comprises aqueous-soluble and aqueous-erodible cellulosics such as ethyl cellulose (EC), methyl ethyl cellulose (MEC), carboxy methyl cellulose (CMC), carboxy methyl ethyl cellulose (CMEC), hydroxy ethyl cellulose (HEC), hydroxy propyl cellulose (HPC), cellulose acetate (CA), cellulose propionate (CP) cellulose butyrate (CB), CAB, CAP, CAT, HPMC, HPMCP, HPMCAS, HPMCAT, and ethylhydroxy ethylcellulose (EHEC) A particularly preferred class of such cellulosics comprises various grades of low viscosity (MW $\leq$ 50,000 daltons) and high viscosity (MW $\geq$ 50,000 daltons) HPMC. Commercially available low viscosity HPMC polymers include the Dow METHOCEL™ series E5, E15LV, E50LV and K100LY, while high viscosity HPMC polymers include E4MCR, E10MCR, K4M, K15M and K100M; especially preferred in this group are the METHOCEL™ K series. Other commercially available types of HPMC include the Shinetsu METOLOSE 90SH series.

Another useful class of erodible matrix material comprises polyoxamers including polyethylene oxide (PEO), polypropylene oxide (PPO), PEG, PPG, PEG/PPG copolymers, block and random copolymers of ethylene oxide and propylene oxide. Examples of commercial grades of such materials are the polyoxamers sold by BASF Corporation of Parsippany, N.J. under the names LUTROL and PLURONIC; and those polyethylene glycols and polyethylene oxides sold under the names POLYOX and MACROGEL. A particularly useful family of polymers in this class are the polyoxyethylenes having an average MW ranging from 50,000 to 6,000,000 daltons sold under the name POLYOX by Union Carbide of Danbury, Conn.

Other materials useful as the erodible matrix material include, but are not limited to polyvinyl pyrrolidone, polyvinyl alcohol, polyvinyl acetate, glycerol fatty acid esters, polyacrylamide, polyacrylic acid, copolymers of ethacrylic acid or methacrylic acid (EUDRAGIT™) and other acrylic acid derivatives such as homopolymers and copolymers of butylmethacrylate, methylmethacrylate, ethylmethacrylate, ethylacrylate, (2-dimethylaminoethyl)methacrylate, and (trimethylaminoethyl) methacrylate chloride.

The erodible matrix polymer may contain a wide variety of the same types of additives and excipients known in the pharmaceutical arts and discussed above, including osmopolymers, osmagens, solubility-enhancing or -retarding agents and excipients that promote stability or processing of the dosage form. The erodible matrix may also be overcoated with one or more pH-sensitive "enteric" or "quasi-enteric" coatings of the types discussed above so as to delay the release of Drug A.

Controlled Release by Extrusion

Controlled release "extrusion" delivery dosage forms of the Drug A compositions of the present invention may be formed, said forms having two components: (1) a core containing an osmotic agent and Drug A composition; and (2) a non-dissolving and non-eroding coating surrounding the core, the coating controlling the influx of water to the core from an aqueous environment of use so as to cause drug release by extrusion of some or all of the core to the environment of use, all as set forth in greater detail in commonly assigned and copending application Ser. No. 09/495,061 filed Jan. 31, 2000, and claiming the priority of Provisional Application Ser. No. 60/119,406 filed Feb. 10, 1999, the pertinent disclosure of which is incorporated herein by reference.

Such dosage forms are specifically designed to provide controlled release of Drug A by an extrusion-type mechanism. The term "extrusion" as it relates to drug delivery mechanism is intended to convey an expulsion or forcing out of some or all of the core through at least one delivery port, or by erosion of the mass of the device. By "at least one delivery port" is meant one or more holes, slits, passageways, channels or pores that may range in size from 10 to more than 5000 µm in diameter that permit release of drug from the dosage form. The drug is delivered primarily by the extrusion of a suspension of solids in water. However, to the extent dissolution has taken place in the core, a portion of Drug A may be delivered as a solution of Drug A.

The form of the device may be any conventional form, including a tablet, a capsule, a caplet, a bead, a multiparticulate, powders for suspension or unit dosage packages or combinations thereof. Drug A is released to the environment of use such as the gastro-intestinal (GI) tract as a result of the influx of water into the core and the resulting extrusion of an aqueous solution or suspension of Drug A through one or more delivery ports or pores in the coating.

The core of such an extrusion delivery dosage form comprises a Drug A composition of the invention and an osmotic agent such as one or more osmogens and/or osmopolymers, and optionally contains solubility-enhancing agents and excipients. The coating is preferably polymeric, is water-permeable, has at least one delivery port therein and does not dissolve or erode in the environment of use.

Alternatively, the core may comprise only an amorphous form of Drug A, that core being coated with the non-eroding coating bearing the delivery port(s), and then overcoated with all or part of the concentration-enhancing polymer.

By "osmotic agent" is meant any agent which creates a driving force for transport of water from the environment of use into the core of the device. Exemplary osmotic agents are water-swellable hydrophilic polymers, and osmogens (or osmagens). Thus, the core may include water-swellable hydrophilic polymers, both ionic and nonionic, often referred to as "osmopolymers" and "hydrogels."

The amount of water-swellable hydrophilic polymers present in the core may range from about 5 to about 80 wt %, preferably 10 to 50 wt %. Exemplary materials include hydrophilic vinyl and acrylic polymers, polysaccharides such as calcium alginate, polyethylene oxide (PEO), polyethylene glycol (PEG), polypropylene glycol (PPG), poly (2-hydroxyethyl methacrylate), poly(acrylic) acid, poly (methacrylic) acid, PVP and crosslinked PVP, PVA, PVA/PVP copolymers and PVA/PVP copolymers with hydrophobic monomers such as methyl methacrylate, vinyl acetate, and the like, hydrophilic polyurethanes containing large PEO blocks, sodium croscarmelose, carrageenan, HEC, HPC, HPMC, CMC and CEC, sodium alginate, polycarbophil, gelatin, xanthan gum, and sodium starch glycolate.

Other osmotic agent materials include hydrogels comprising interpenetrating networks of polymers which may be formed by addition or by condensation polymerization, the components of which may comprise hydrophilic and hydrophobic monomers such as those just mentioned. Preferred polymers for use as the water-swellable hydrophilic polymers include PEO, PEG, PVP, sodium croscarmelose, HPMC, sodium starch glycolate, polyacrylic acid and crosslinked versions thereof. In one embodiment of the invention the osmotic agent and the concentration-enhancing polymer in the composition of Drug A can comprise the same polymeric material.

The core may also contain osmotically effective solutes. By "osmotically effective solutes," is meant any water-soluble compound that is commonly referred to in the pharmaceutical arts as an "osmogen" or an "osmagent." The amount of osmogen present in the core may range from about 2 to about 70 wt %, preferably 10 to 50 wt %. Typical classes of suitable osmogens are water-soluble organic acids, salts and sugars that are capable of imbibing water to thereby effect an osmotic pressure gradient across the barrier of the surrounding coating. Typical useful osmogens include magnesium sulfate, magnesium chloride, calcium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, glucose, fructose, citric acid, succinic acid, and mixtures thereof. Particularly preferred osmogens are glucose, lactose, sucrose, mannitol, xylitol and sodium chloride.

The essential constraints on the coating for the extrusion delivery device are that it be water-permeable, have high strength, be easily manufactured, have at least one port for the delivery of drug, and be non-dissolving and non-eroding during release of the drug formulation. The goal to be achieved by such an extrusion delivery device is to substantially entirely deliver Drug A through the delivery port(s) or pores as opposed to delivery via permeation through the coating material itself.

Coatings may be dense, microporous or "asymmetric," having a dense region supported by a thick porous region such as those disclosed in U.S. Pat. Nos. 5,612,059 and 5,698,220. When the coating is dense the coating is composed of a water-permeable material. When the coating is porous, it may be composed of either a water-permeable or a water-impermeable material. When the coating is composed of a porous water-impermeable material, water permeates through the pores of the coating as either a liquid or a vapor.

Examples of osmotic devices that utilize such dense coatings include U.S. Pat. Nos. 3,995,631 and 3,845,770, the disclosures of which pertaining to dense coatings are incorporated herein by reference. Such dense coatings are permeable to the external fluid such as water and may be composed of any of the materials mentioned in these patents as well as other water-permeable polymers known in the art.

The membranes may also be porous as disclosed in U.S. Pat. Nos. 5,654,005 and 5,458,887 or even be formed from water-resistant polymers. U.S. Pat. No. 5,120,548 describes another suitable process for forming coatings from a mixture of a water-insoluble polymer and a leachable water-soluble additive, the pertinent disclosures of which are incorporated herein by reference. The porous membranes may also be formed by the addition of pore-formers as disclosed in U.S. Pat. No. 4,612,008, the pertinent disclosures of which are incorporated herein by reference.

In addition, vapor-permeable coatings may even be formed from extremely hydrophobic materials such as polyethylene or polyvinylidenefluoride that, when dense, are essentially water-impermeable, as long as such coatings are porous. Such coatings are disclosed in U.S. Pat. No. 5,798,119, the pertinent disclosure of which is incorporated herein by reference. Processes for forming such coatings are disclosed in U.S. Pat. Nos. 4,247,498, 4,490,431 and 4,744,906, the disclosures of which are also incorporated herein by reference.

Materials useful in forming the coating include various grades of acrylics, vinyls, ethers, polyamides, polyesters and cellulosic derivatives that are water-permeable and water-insoluble at physiologically relevant pHs, or are susceptible to being rendered water-insoluble by chemical alteration such as by crosslinking.

Specific examples of suitable polymers (or crosslinked versions) useful in forming the coating include plasticized, unplasticized and reinforced cellulose acetate (CA), cellulose diacetate, cellulose triacetate, CA propionate, cellulose nitrate, CA butyrate (CAB), CA ethyl carbamate, CAP, CA methyl carbamate, CA succinate, CA trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylene-vinylacetate, EC, PEG, PPG, PEG/PPG copolymers, PVP, HEC, HPC, CMC, CMEC, HPMC, HPMCP, HPMCAS, HPMACT, poly(acrylic) acids and esters and poly-(methacrylic) acids and esters and copolymers thereof, starch, dextran, dextrin, chitin, chitosan, collagen, gelatin, polyalkenes, polyethers, polysulfones, polyethersulfones, polystyrenes, polyvinyl halides, polyvinyl esters and ethers, natural waxes and synthetic waxes.

A preferred coating composition comprises a cellulosic polymer, in particular cellulose ethers, cellulose esters and cellulose ester-ethers, i.e., cellulosic derivatives having a mixture of ester and ether substituents, such as HPMCP.

Another preferred class of coating materials are poly (acrylic) acids and esters, poly(methacrylic) acids and esters, and copolymers thereof.

Particularly suitable polymers include cellulose acetate, cellulose acetate butyrate, and ethyl cellulose. A particularly preferred set of polymers are cellulose acetates having acetyl contents of 25 to 42%. A preferred polymer is CA having an acetyl content of 39.8%, and specifically, CA 398-10 manufactured by Eastman of Kingsport, Tenn., having an average molecular weight of about 40,000 daltons. Another preferred CA having an acetyl content of 39.8% is high molecular weight CA having an average molecular weight greater than about 45,000, and specifically, CA 398-30 (Eastman) reported to have an average molecular weight of 50,000 daltons. The high molecular weight CA provides superior coating strength, which allows thinner coatings and thus higher permeability.

Coating is conducted in conventional fashion by first forming a coating solution and then coating by dipping, fluidized bed coating, or preferably by pan coating. To accomplish this, a coating solution is formed comprising the coating polymer and a solvent. Typical solvents useful with the cellulosic polymers noted above include acetone, methyl acetate, ethyl acetate, isopropyl acetate, n-butyl acetate, methyl isobutyl ketone, methyl propyl ketone, ethylene glycol monoethyl ether, ethylene glycol monoethyl acetate, methylene dichloride, ethylene dichloride, propylene dichloride, nitroethane, nitropropane, tetrachloroethane, 1,4-dioxane, tetrahydrofuran, diglyme, and mixtures thereof. A particularly preferred solvent is acetone. The coating solution typically will contain 3 to 15 wt % of the polymer, preferably 5 to 10 wt %, most preferably 7 to 10 wt %.

The coating solution may also comprise pore-formers, non-solvents (defined below), or plasticizers in any amount so long as the polymer remains substantially soluble at the conditions used to form the coating and so long as the coating remains water-permeable and has sufficient strength. Pore-formers and their use in fabricating coatings are described in U.S. Pat. Nos. 5,612,059 and 5,698,220, the pertinent disclosures of which are incorporated herein. The term "pore former," as used herein, refers to a material added to the coating solution that has low or no volatility relative to the solvent such that it remains as part of the coating following the coating process but that is sufficiently water swellable or water soluble such that, in the aqueous use environment it provides a water-filled or water-swollen channel or "pore" to allow the passage of water thereby enhancing the water permeability of the coating. Suitable pore-formers include polyethylene glycol (PEG), PVP, PEO, HEC, HPMC and other aqueous-soluble cellulosics, water-soluble acrylate or methacrylate esters, polyacrylic acid and various copolymers and mixtures of these water soluble or water swellable polymers.

By "non-solvent" is meant any material added to the coating solution that substantially dissolves in the coating solution and reduces the solubility of the coating polymer or polymers in the solvent. In general, the function of the non-solvent is to impart porosity to the resulting coating. As described below, porous coatings have higher water permeability than an equivalent weight of a coating of the same composition that is not porous. This porosity, when the pores are gas filled, as is typical when the non-solvent is volatile, is indicated by a reduction in the density of the coating (mass/volume). Although not wishing to be bound by any particular mechanism of pore formation, it is generally believed that addition of a non-solvent imparts porosity to the coating during evaporation of solvent by causing the coating solution to undergo liquid-liquid phase separation prior to solidification. As described below for the case of using water as the non-solvent in an acetone solution of cellulose acetate, the suitability and amount of a particular candidate material can be evaluated for use as a non-solvent by progressively adding the candidate non-solvent to the coating solution until it becomes cloudy. If this does not occur at any addition level up to about 50 wt % of the coating solution, it generally is not appropriate for use as a non-solvent. When clouding is observed, termed the "cloud point," an appropriate level of non-solvent for maximum porosity is the amount just below the cloud point. When lower porosities are desired, the amount of non-solvent can be reduced as low as desired. It has been found that suitable coatings can be obtained when the concentration of non-solvent in the coating solution is greater than about 20% of the non-solvent concentration that results in the cloud point.

Suitable non-solvents are any materials that have appreciable solubility in the solvent and that lower the coating polymer solubility in the solvent. The preferred non-solvent depends on the solvent and the coating polymer chosen. In the case of using a volatile polar coating solvent such as acetone or methyl ethyl ketone, suitable non-solvents include water, glycerol, ethylene glycol and its low molecular-weight oligomers (e.g., less than about 1,000 daltons), propylene glycol and its low molecular weight oligomers (e.g., less than about 1,000 daltons), $C_1$ to $C_4$ alcohols such as methanol or ethanol, ethylacetate, acetonitrile and the like.

In general, to maximize its effect, (e.g., formation of pores), the non-solvent should have similar or less volatility than the coating solution solvent such that, during initial evaporation of the solvent during the coating process, sufficient non-solvent remains to cause phase separation to occur. In many cases, where a coating solution solvent such as acetone is used, water is a suitable non-solvent. For acetone solutions comprising 7 wt % CA and 3 wt % PEG, the cloud point at room temperature is at about 23 wt % water. Thus the porosity and in turn the water permeability (which increases with increasing porosity) can be controlled by varying the water concentration up to near the cloud point. For acetone solutions comprising CA and PEG with a total concentration of about 10 wt %, it is desired that the coating solution contain at least 4 wt % water to obtain a suitable coating. When a higher porosity, and thus a higher water permeability is desired (to obtain a faster release rate), the coating solution should contain at least about 15 wt % water.

In one embodiment of the invention, the coating solution is homogeneous, in that when the polymer, solvent, and any pore formers or non-solvents are mixed, the solution comprises a single phase. Typically, a homogenous solution will be clear, and not be cloudy as discussed above.

When using CA 398-10, exemplary coating solution weight ratios of CA:PEG 3350:water are 7:3:5, 8:2:5, and 9:1:5, with the remainder of the solution comprising a solvent such as acetone. Thus, for example, in a solution having a weight ratio of CA:PEG 3350:water of 7:3:5, CA comprises 7 wt % of the solution, PEG 3350 comprises 3 wt % of the solution, water comprises 5 wt % of the solution, and acetone comprises the remaining 85 wt %.

The coating can optionally include a plasticizer. A plasticizer generally swells the coating polymer such that the polymer's glass transition temperature is lowered, its flexibility and toughness increased and its permeability altered. When the plasticizer is hydrophilic, such as polyethylene glycol, the water permeability of the coating is generally increased. When the plasticizer is hydrophobic, such as diethyl phthalate or dibutyl sebacate, the water permeability of the coating is generally decreased.

It should be noted that additives can function in more than one way when added to the coating solution. For example, PEG can function as a plasticizer at low levels while at higher levels it can form a separate phase and act as a pore former. In addition, when a non-solvent is added, PEG can also facilitate pore formation by partitioning into the non-solvent-rich phase once liquid-liquid phase separation occurs.

The weight of the coating around the core depends on the composition and porosity of the coating, the surface to volume ratio of the dosage form, and the desired drug release rate, but generally should be present in an amount ranging from about 3 to 30 wt %, preferably from 8 to 25 wt %, based on the weight of the uncoated core. However, a coating weight of at least about 8 wt % is generally preferred so as to assure sufficient strength for reliable performance, and more preferably a coating greater than about 13 wt %.

While porous coatings based on CA, PEG, and water yield excellent results, other pharmaceutically acceptable materials may be used so long as the coating has the requisite combination of high water permeability, high strength, and ease of manufacture. Further, such coatings may be dense, or asymmetric, having one or more dense layers and one or more porous layers, as described in U.S. Pat. Nos. 5,612,059 and 5,698,220.

The coating must also contain at least one delivery port in communication with the interior and exterior of the coating to allow for release of the drug-containing composition to the exterior of the dosage form. The delivery port can range in size from about the size of the drug particles, and thus could be as small as 10 to 100 microns in diameter and may be termed pores, up to about 5000 microns in diameter. The shape of the port may be substantially circular, in the form of a slit, or other convenient shape to ease manufacturing and processing. The port(s) may be formed by post-coating mechanical or thermal means or with a beam of light (e.g., a laser), a beam of particles, or other high-energy source, or may be formed in situ by rupture of a small portion of the coating. Such rupture may be controlled by intentionally incorporating a relatively small weak portion into the coating. Delivery ports may also be formed in situ by erosion of a plug of water-soluble material or by rupture of a thinner portion of the coating over an indentation in the core. Delivery ports may be formed by coating the core such that one or more small regions remains uncoated. In addition, the delivery port can be a large number of holes or pores that may be formed during coating, as in the case of asymmetric membrane coatings of the type disclosed in U.S. Pat. Nos. 5,612,059 and 5,698,220, the disclosures of which are incorporated by reference. When the delivery pathways are pores there can be a multitude of such pores that range in size from 10 μm to greater than 100 μm. During operation, one or more of such pores may enlarge under the influence of the hydrostatic pressure generated during operation. The number of delivery ports may vary from 1 to 10 or more. In aggregate, the total surface area of core exposed by delivery ports is less than 5%, and more typically less than 1%.

A preferred embodiment of osmotic delivery devices consists of a Drug A layer containing one of the pharmaceutical compositions of the present invention and a sweller layer that comprises a water-swellable polymer, with a coating surrounding the drug and sweller layer, all as set forth in commonly assigned Provisional Application Ser. No. 60/171,968, filed Dec. 23, 1999, the disclosure of which is incorporated herein by reference. Each layer may contain other excipients such as tableting aids, osmagens, surfactants, water-soluble polymers and water-swellable polymers.

When placed in an aqueous medium, the tablet imbibes water through the membrane, causing the composition to form a dispensable aqueous composition, and causing the hydrogel/sweller layer to expand and push against the Drug A-containing composition, forcing the composition out the delivery port. The composition can swell, aiding in forcing Drug A out the delivery port. Drug A can be delivered from this type of delivery system either dissolved or dispersed in the composition that is expelled from the delivery port.

The rate of drug delivery is controlled by such factors as the permeability and thickness of the coating, the osmotic pressure of the drug-containing layer, the degree of hydrophilicity of the hydrogel/sweller layer, and the surface area of the device. Those skilled in the art will appreciate that increasing the thickness of the coating will reduce the release rate, while any of the following will increase the release rate: increasing the permeability of the coating; increasing the hydrophilicity of the hydrogel layer; increasing the osmotic pressure of the drug-containing layer; or increasing the device's surface area.

Exemplary materials useful in forming the Drug A-containing pharmaceutical composition, in addition to the pharmaceutical composition itself, include HPMC, PEO and PVP and other pharmaceutically acceptable carriers. In addition, osmagents such as sugars or salts, especially sucrose, lactose, sucrose, mannitol, or sodium chloride, may be added. Materials which are useful for forming the hydrogel/sweller layer include sodium CMC, PEO, poly (acrylic acid), sodium (polyacrylate), sodium starch glycolate, PVP, crosslinked PVP, and other high molecular weight hydrophilic materials. Particularly useful are PEO polymers having an average molecular weight from about 5,000,000 to about 7,500,000 Daltons.

In the case of a bilayer geometry, the delivery port(s) or exit passageway(s) may be located on the side of the tablet containing the drug composition or may be on both sides of the tablet or even on the edge of the tablet so as to connect both the drug layer and the sweller layer with the exterior of the device. The exit passageway(s) may be produced by mechanical means or by laser drilling, or by creating a difficult-to-coat region on the tablet by use of special tooling during tablet compression or by other means. The rate of Drug A delivery from the device may be optimized so as to provide a drug release profile for optimum therapeutic effect.

Another embodiment of sustained release osmotic dosage forms of the invention includes Drug A-containing multiparticulates coated with a water-permeable membrane; the polymer may be dense, porous or asymmetric as described above. Such multiparticulates are prepared by, for example, melt congealing from a spinning disk, extrusion/spheronization or fluid bed granulation, or by coating nonpareil seeds with a mixture of drug and a water-soluble polymer, as described above. Drug A-containing multiparticulates are then spray-coated with a solution of a polymer in a mixture of a solvent and, depending on the coating type desired, may contain a non-solvent, as described above. This spray-coating operation is preferably carried out in a fluid bed coating apparatus, for example, a Glatt GPCG-5 fluid bed coater (Glatt Air, Ramsey, N.J.). The polymer used for forming the semipermeable membrane is chosen as described above.

Drug A is primarily released from such multiparticulates following rupture of the coating and, following rupture, such release may be gradual or relatively sudden. When the collection of beads has a variable composition, the composition may be chosen such that the beads rupture at various times following ingestion, resulting in the overall release of drug being sustained for a desired duration.

Extrusion capsules can be made using the same or similar components to those described above for osmotic tablets and multiparticulates. The capsule shell or portion of the capsule shell can be semipermeable and made of materials described above. The capsule can then be filled either by a powder or liquid consisting of Drug A-containing composition, excipients that imbibe water to provide osmotic potential, and/or a water-swellable polymer optionally solubilizing excipients. The capsule core can also be made such that it has a bilayer or multilayer composition analogous to the bilayer geometry described above.

For any of the controlled or sustained-release dosage forms mentioned above, the dosage form may additionally comprise an immediate-release layer of Drug A or a different drug in crystalline, amorphous or dispersion form.

Other features and embodiments of the invention will become apparent from the following examples which are given for illustration of the invention rather than for limiting its intended scope.

EXAMPLE 1

An amorphous solid dispersion of 25 wt % Drug A and 75 wt % polymer was made by first mixing Drug A in the solvent acetone together with a finely powdered "MF" grade of the cellulosic polymer HPMCAS (AQUOT-MF, Shin-Etsu Chemical Co., Ltd., Tokyo, Japan) to form a solution. The solution comprised 1.25 wt % Drug A, 3.75 wt % HPMCAS-MF, and 95 wt % acetone. This solution was then spray-dried by directing an atomizing spray via a 2-fluid external mix spray nozzle at 2.6 bar (37 psig) at a 175 to 180 g/min feed rate into a stainless steel chamber of a NIRO XP spray drier, maintained at a temperature of 180° C. at the inlet and 69° at the outlet.

The resulting amorphous solid dispersion was collected via a cyclone and then dried in a Gruenberg solvent tray dryer by spreading the spray-dried particles onto polyethylene-lined trays to a depth of a little less than 1 cm, and then drying them at 40° C. for 8 hours.

EXAMPLE 2

An amorphous solid dispersion was prepared as in Example 1 except that the dispersion was prepared by a NIRO PSD-1 spray-dryer using the same operating parameters as in Example 1, and the dispersion contained 50 wt % Drug A and 50 wt % HPMCAS-MF and the spray solution comprised 1.25 wt % Drug A, 1.25 wt % HPMCAS-MF, 97.5 wt % acetone.

EXAMPLES 3–7

Amorphous solid dispersions were prepared following the procedure of Example 1 except that a "mini" spray-dryer was used and the polymers used for the dispersions were HPMC, PVP, CAP, CAT and HPMCP, respectively. The "mini" spray dryer, consisted of an atomizer in the top cap of a vertically oriented stainless steel pipe. The atomizer was a two-fluid nozzle (Spraying Systems Co. 1650 fluid cap and 64 air cap) where the atomizing gas was nitrogen delivered to the nozzle at 100° C. and a flux of 15 gm/min, and the test solution to be spray dried was delivered to the nozzle at room temperature and a flow rate of 1 gm/min using a syringe pump. Filter paper with a supporting screen was clamped to the bottom end of the pipe to collect the solid spray-dried material and allow the nitrogen and evaporated solvent to escape.

EXAMPLE 8

An amorphous solid dispersion containing 50 wt % Drug A and 50 wt % HPMCAS-MF in acetone was formed by roto-evaporating the Drug A/HPMCAS-MF solution to dryness. The solution consisted of 7.5% Drug A, 7.5% HPMCAS-MF, 80.75 wt % acetone, and 4.25% water. The dispersion was placed under a vacuum for 20 hours, followed by storage in a dessicator.

EXAMPLE 9

An amorphous solid dispersion was formed by triturating 50 wt % Drug A with 50 wt % HPMCAS-MF by dry mixing 3.6 mg amorphous Drug A with 3.6 mg HPMCAS-MF on a vortex mixer for 1 minute.

EXAMPLE 10

A solution comprising 2.5 wt % Drug A, 7.5 wt % HPMCAS-MF, and 90 wt % solvent (5 wt % water in acetone) was spray-coated onto NU-CORE sugar non-pariel beads having a 45/60 mesh, resulting in a coating of an amorphous solid dispersion of Drug A and HPMCAS-MF on the surface of the beads. An analysis showed that the coated beads contained 3.9 wt % Drug A.

EXAMPLE 11

A solution comprising 7.5 wt % HPMCAS-MF dissolved in 92.5 wt % solvent (5 wt % water in acetone) was prepared and spray-coated onto NU-CORE beads having a 45/60 mesh, resulting in a thin coating of the HPMCAS-MF on the surface of the beads.

Controls 1 and 2 were formed, comprising 3.6 mg of crystalline Drug A and an equal amount of non-dispersed amorphous Drug A, respectively.

EXAMPLE 12

In Vitro Drug Dissolution

The compositions of Examples 1–9 and Controls 1 and 2 were evaluated by in vitro dissolution tests with a microcentrifuge method using a dosage of 2000 μgA/mL of each of the dispersions and controls in microcentrifuge tubes. The term "μgA" refers to the weight in micrograms of active Drug A. The tubes were each placed in a 37° C. sonicating bath, and 1.8 mL of a phosphate buffered solution (PBS) was added, the PBS solution comprising 20 mM $NaH_2PO_4$, 47 mM $KH_2PO_4$, 87 mM NaCl and 0.2 mM KCl, adjusted to pH 6.5 and having an osmotic pressure of 290 mOsm/kg. The samples were mixed using a vortex mixer for about 60 seconds, then microcentrifuged at 13,000 G at 37° C. for 1 minute. The resulting supernatant solution for each was then sampled and diluted 1:6 by volume with methanol, then analyzed by HPLC. The contents of the tubes were then mixed on the vortex mixer and allowed to stand undisturbed at 37° C. until the next sample was taken. Samples were collected at 4, 10, 20, 40, 90, and 1200 minutes. The results of such dissolution tests are shown in Table 1.

The performance of the spray-coated beads of Example 10 was tested using the same microcentrifuge method, except that 2.5 g of the coated beads were added to 50 mL of PBS solution, resulting in a dosage of 2000 μgA/mL. The results of these dissolution tests are also shown in Table 1.

A microcentrifuge dissolution test was also performed by mixing samples of the coated beads of Example 11 with 100 mg of amorphous Drug A in 50 mL of PBS solution to yield a dosage of 2000 μgA/mL. The results of these dissolution tests are also shown in Table 1.

For Controls 1 and 2, in vitro dissolution tests were also performed using the same microcentrifuge method except that 3.6 mg of crystalline and amorphous Drug A was used, respectively, resulting in a dosage of 2000 μgA/mL. The results of the dissolution tests are shown in Table 1.

TABLE 1

| Example No. | Time (min) | [Drug A]* | AUC** |
|---|---|---|---|
| 1 | 0 | 0 | 0 |
|  | 4 | 635 | 1,300 |
|  | 10 | 644 | 5,100 |
|  | 20 | 711 | 11,900 |
|  | 40 | 769 | 26,700 |
|  | 90 | 844 | 67,000 |
|  | 1200 | 1290 | 1,251,400 |
| 2 | 0 | 0 | 0 |
|  | 4 | 601 | 1,200 |
|  | 10 | 625 | 4,900 |
|  | 20 | 653 | 11,300 |
|  | 40 | 624 | 24,000 |
|  | 90 | 693 | 57,000 |
|  | 1200 | 548 | 745,700 |
| 3 | 0 | 0 | 0 |
|  | 3 | 544 | 1,100 |
|  | 10 | 558 | 4,400 |
|  | 20 | 558 | 10,000 |
|  | 40 | 552 | 21,100 |
|  | 90 | 565 | 49,300 |
|  | 1200 | 397 | 582,900 |
| 4 | 0 | 0 | 0 |
|  | 3 | 526 | 1,100 |
|  | 10 | 637 | 4,500 |
|  | 20 | 649 | 11,000 |
|  | 40 | 651 | 24,000 |
|  | 90 | 688 | 57,800 |
|  | 1200 | 409 | 666,300 |
| 5 | 0 | 0 | 0 |
|  | 3 | 2066 | 4,100 |
|  | 10 | 2035 | 16,400 |
|  | 20 | 2075 | 37,000 |
|  | 40 | 1965 | 77,400 |
|  | 90 | 1845 | 172,600 |
|  | 1200 | 255 | 1,338,100 |
| 6 | 0 | 0 | 0 |
|  | 3 | 2040 | 4,100 |
|  | 10 | 1777 | 15,500 |
|  | 20 | 1704 | 32,900 |
|  | 40 | 1483 | 64,800 |
|  | 90 | 427 | 113,400 |
|  | 1200 | 257 | 492,200 |
| 7 | 0 | 0 | 0 |
|  | 3 | 1036 | 2,100 |
|  | 10 | 1277 | 9,000 |
|  | 20 | 1246 | 21,600 |
|  | 40 | 1217 | 46,300 |
|  | 90 | 503 | 89,900 |
|  | 1200 | 350 | 562,700 |
| 8 | 0 | 0 | 0 |
|  | 4 | 134 | 270 |
|  | 10 | 197 | 1,300 |
|  | 20 | 248 | 3,500 |
|  | 40 | 308 | 9,000 |
|  | 90 | 378 | 26,200 |
|  | 1200 | 591 | 564,000 |
| 9 | 0 | 0 | 0 |
|  | 4 | 929 | 1,900 |
|  | 10 | 927 | 7,400 |
|  | 20 | 932 | 16,700 |
|  | 40 | 980 | 35,800 |
|  | 90 | 957 | 84,300 |
|  | 1200 | 720 | 1,015,000 |
| 10 | 0 | 0 | 0 |
|  | 4 | 412 | 800 |
|  | 10 | 491 | 3,500 |
|  | 20 | 523 | 8,600 |
|  | 40 | 561 | 19,400 |
|  | 90 | 617 | 48,900 |
|  | 180 | 752 | 110,500 |
|  | 1200 | 967 | 928,000 |
| 11 | 0 | 0 | 0 |
|  | 4 | 797 | 1,600 |
|  | 10 | 1047 | 7,100 |
|  | 20 | 1292 | 18,800 |
|  | 40 | 1523 | 47,000 |
|  | 90 | 1653 | 126,400 |
|  | 180 | 1724 | 278,300 |
|  | 1200 | 1882 | 2,088,300 |
| Control 1 (Crystalline Drug A) | 0 | 0 | 0 |
|  | 4 | 130 | 260 |
|  | 10 | 149 | 1,100 |
|  | 20 | 139 | 2,500 |
|  | 40 | 149 | 5,400 |
|  | 90 | 147 | 12,800 |
|  | 1200 | 125 | 163,800 |
| Control 2 (Amorphous Drug A) | 0 | 0 | 0 |
|  | 4 | 586 | 1,200 |
|  | 10 | 473 | 4,300 |
|  | 20 | 220 | 7,800 |
|  | 40 | 182 | 11,800 |
|  | 90 | 167 | 20,600 |
|  | 180 | 158 | 35,100 |
|  | 1200 | 203 | 225,900 |

*μgA/mL
**min · μgA/mL

The overall results of these dissolution tests are summarized in Table 2, giving the maximum concentration of Drug A in solution during the first 90 minutes of the test ($c_{max90}$), the area under the aqueous concentration vs. time curve after 90 minutes ($AUC_{90}$) and the concentration at 1200 minutes ($c_{1200}$).

The results show that the performance of the compositions of Examples 1–11 was much better than that of crystalline Drug A alone (Control 1), with $C_{max90}$ values ranging from 2.5- to nearly 14-fold that of Control 1, and $AUC_{90}$ values ranging from 2- to 13.5-fold that of Control 1. With respect to the amorphous Drug A alone, the compositions of Examples 1–11 demonstrated $AUC_{90}$ values that were 1.3- to 8.4-fold that of Control 2.

TABLE 2

| Example No. | Polymer | wt % Drug A in Dispersion | $c_{max90}$* | $AUC_{90}$** | $c_{1200}$* |
|---|---|---|---|---|---|
| 1 | HPMCAS-MF | 25 | 844 | 67,000 | 1290 |
| 2 | HPMCAS-MF | 50 | 987 | 79,600 | 1707 |
| 3 | HPMC | 25 | 565 | 49,300 | 397 |
| 4 | PVP | 25 | 688 | 57,800 | 409 |
| 5 | CAP | 25 | 2075 | 173,600 | 255 |
| 6 | CAT | 25 | 2040 | 113,400 | 257 |
| 7 | HPMCP | 25 | 1277 | 89,900 | 350 |
| 8 | HPMCAS-MF | 50 | 378 | 26,200 | 591 |
| 9 | HPMCAS-MF | 50 | 980 | 84,300 | 720 |
| 10 | HPMCAS-MF | 25 | 617 | 48,900 | 967 |
| 11 | HPMCAS-MF | — | 1653 | 126,400 | 1882 |
| Control 1 (Crystalline Drug A) | NONE | 0 | 149 | 12,800 | 125 |
| Control 2 (Amorphous Drug A) | NONE | 0 | 586 | 20,600 | 203 |

*µgA/mL
**min · µgA/mL

EXAMPLES 13–15

Amorphous dispersions of 50 wt % Drug A and 50 wt % HPMCAS-MF were made by first mixing Drug A in a solvent comprising 5 wt % water in acetone together with HPMCAS-MF to form a solution. The solution comprised 7.5 wt % Drug A, 7.5 wt % HPMCAS, 4.25 wt % water, and 80.75 wt % acetone. This solution was spray-dried by directing an atomizing spray with a nozzle at 2.7 bar at a feed rate of 100 g/min into the stainless steel chamber of a Niro PSD-1 spray-dryer, maintained at a temperature of 140° C. at the inlet and 70° C. at the outlet.

Three different nozzles were used to form the dispersions under the conditions described above. A fountain nozzle was used in Example 13, a Niro two-fluid nozzle in Example 14, and a flat fan nozzle in Example 15, the nozzles having the specifications noted in the section above entitled "Methods of Forming Dispersion."

The amorphous solid dispersions were collected via a cyclone and then dried in a Gruenberg solvent tray-dryer by spreading the spray-dried particles onto polyethylene-lined trays to a depth of not more than 1 cm and then drying them at 40° C. for at least 12 hours.

In vitro dissolution tests were performed as described in Example 12 for the dispersions formed with the three nozzle types. The results of such tests are shown in Table 3 and summarized in Table 4.

TABLE 3

| Example No. | Time (mins) | [Drug A]* | Dosage* | $c_{max,90}$* | AUC** |
|---|---|---|---|---|---|
| 13 (fountain) | 0 | 0 | 1980 | | 0 |
| | 4 | 736 | | | 1,500 |
| | 10 | 650 | | | 5,600 |
| | 20 | 593 | | | 11,800 |
| | 40 | 624 | | | 24,000 |
| | 90 | 651 | | 736 | 55,900 |
| 14 (two-fluid) | 0 | 0 | 1905 | | 0 |
| | 4 | 615 | | | 1,200 |
| | 10 | 559 | | | 4,800 |
| | 20 | 579 | | | 10,400 |
| | 40 | 579 | | | 22,000 |
| | 90 | 545 | | 615 | 50,100 |
| 15 (flat fan) | 0 | 0 | 1954 | | 0 |
| | 4 | 684 | | | 1,400 |
| | 10 | 645 | | | 5,400 |
| | 20 | 599 | | | 11,600 |
| | 40 | 596 | | | 23,500 |
| | 90 | 597 | | 684 | 53,300 |

*µgA/mL
**min · µgA/mL

TABLE 4

| Example No. | Nozzle Type | $C_{max,90}$* | $AUC_{90}$** | $C_{1200}$* |
|---|---|---|---|---|
| 13 | fountain | 736 | 55,900 | 460 |
| 14 | two-fluid | 615 | 50,100 | 543 |
| 15 | flat fan | 684 | 53,300 | 432 |

*µgA/mL
**min · µgA/mL

EXAMPLE 16

Amorphous solid dispersions of 50 wt % Drug A and 50 wt % HPMCAS-MF were made as in Example 2 using the same type of two-fluid nozzle spray-dryer and varying the inlet ($T_{in}$) and outlet ($T_{out}$) temperatures as shown in Table 5. The spray solution was 7.5 wt % Drug A, 7.5 wt % HPMCAS-MF, 80.75 wt % acetone, and 4.25 wt % water.

TABLE 5

| $T_{in}$ (° C.) | $T_{out}$ (° C.) |
|---|---|
| 130 | 70 |
| 140 | 70 |
| 145 | 70 |
| 165 | 70 |
| 175 | 70 |
| 195 | 70 |
| 140 | 60 |
| 140 | 50 |
| 120 | 40 |
| 175 | 60 |
| 175 | 50 |

EXAMPLE 17

An amorphous solid dispersion of 50 wt % Drug A and 50 wt % HPMCAS-MF was made by first mixing Drug A with HPMCAS in a solvent. A spray solution comprising 7.5 wt % Drug A, 7.5 wt % HPMCAS-MF, 80.75 wt % acetone, and 4.25 wt % water was spray-dried by directing an atomizing spray with a two-fluid nozzle at 2.7 bar at a feed rate of 200 g/min into the stainless steel chamber of a Niro PSD-1 spray-dryer, maintained at a temperature of 170° C. at the inlet and 60° C. at the outlet.

The resulting dispersion was collected via a cyclone and then dried in a Glatt GPCG1 fluid bed dryer by suspending the spray-dried particles with air and then drying them at 40° C.

The performance of the dispersion was evaluated using in vitro dissolution tests after fluid bed drying. A sample of the dispersion was placed in 20 mL of a simulated gastric solution (10 mM HCl, 100 mM NaCl, pH 1.2), at a concentration of 5 mgA/mL, in a tightly stoppered flask. The flask was attached to a rotating wheel in a 37° C. chamber and rotated at 50 rpm. After 30 minutes, 10 mL of pH 6.5 PBS, at 5 times the standard buffer concentration, was added to produce a final pH of 6.5 and a final volume of 30 mL. Drug concentrations were determined by periodically withdrawing samples, centrifuging the samples to remove any undissolved drug, diluting the supernatant in methanol, analyzing the supernatant by HPLC, and calculating drug concentrations. Results are shown in Table 6.

TABLE 6

| Time (mins) | [Drug A]* | Dosage* | $C_{max,90}$* | $AUC_{90}$** |
|---|---|---|---|---|
| 0 | 0 | 1942 | | 0 |
| 4 | 587 | | | 2,000 |
| 10 | 524 | | | 5,300 |
| 20 | 525 | | | 10,600 |
| 40 | 534 | | | 21,200 |
| 90 | 510 | | 587 | 47,200 |

*µgA/mL
**min · µgA/mL

EXAMPLE 18

This example shows the results of dissolution tests with dispersions containing various grades of HPMCAS manufactured by Shin-Etsu or Eastman Fine Chemicals (Kingsport, Tenn.). HPMCAS grades are designated as "L," "M," or "H," referring to a "low," "medium," or "high" dissolution pH of 5.5, 6.0, or 6.5, respectively. The second letter of the grade designation is either "F," for "fine," (a powder) or "G," for "granulated." Dissolution tests were used to compare Drug A dispersions containing HPMCAS-LF, -MF, or -HF.

Solutions containing 2.5 wt % Drug A, 7.5 wt % polymer, 85.5 wt % acetone, and 4.5 wt % water were prepared. The solutions were pumped into a "mini" spray-dryer apparatus via a syringe pump at a rate of 1.3 mL/min. The polymer solution was atomized through a spray nozzle using a heated stream of nitrogen (100° C.). The resulting amorphous solid dispersions containing 25 wt % Drug A were collected on filter paper at a yield of about 43%. The results of dissolution tests in PBS conducted as in Example 12 are presented in Table 7.

TABLE 7

| Polymer | wt % Drug A in Dispersion | Time (min) | [Drug A]* | Dosage* | $c_{max,90}$* | $AUC_{90}$** |
|---|---|---|---|---|---|---|
| Shin-Etsu HPMCAS-LF | 25 | 0 | 0 | 1875 | | 0 |
| | | 4 | 910 | | | 1,800 |
| | | 10 | 1062 | | | 7,700 |
| | | 20 | 1182 | | | 19,000 |
| | | 40 | 1348 | | | 44,300 |
| | | 90 | 1686 | | 1686 | 120,100 |
| | | 1200 | 838 | | | 1,521,000 |
| Eastman HPMCAS-LF | 25 | 0 | 0 | 1971 | | 0 |
| | | 4 | 1449 | | | 2,900 |
| | | 10 | 1530 | | | 11,800 |
| | | 20 | 1619 | | | 26,600 |
| | | 40 | 1654 | | | 60,300 |
| | | 90 | 1739 | | 1739 | 145,000 |
| | | 1200 | 440 | | | 1,354,500 |
| Shin-Etsu HPMCAS-MF | 25 | 0 | 0 | 1892 | | 0 |
| | | 4 | 548 | | | 1,100 |
| | | 10 | 580 | | | 4,500 |
| | | 20 | 593 | | | 10,300 |
| | | 40 | 632 | | | 22,600 |
| | | 90 | 716 | | 716 | 56,300 |
| | | 1200 | 896 | | | 951,000 |
| Eastman HPMCAS-MF | 25 | 0 | 0 | 1800 | | 0 |
| | | 4 | 736 | | | 1,500 |
| | | 10 | 895 | | | 6,400 |
| | | 20 | 1058 | | | 16,100 |
| | | 40 | 1421 | | | 40,900 |
| | | 90 | 1691 | | 1691 | 118,700 |
| | | 1200 | 1544 | | | 1,914,100 |
| Shin-Etsu HPMCAS-HF | 25 | 0 | 0 | 1897 | | 0 |
| | | 4 | 310 | | | 600 |
| | | 10 | 312 | | | 2,500 |
| | | 20 | 310 | | | 5,600 |
| | | 40 | 319 | | | 11,900 |
| | | 90 | 358 | | 358 | 28,800 |
| | | 1200 | 400 | | | 449,500 |

TABLE 7-continued

| Polymer | wt % Drug A in Dispersion | Time (min) | [Drug A]* | Dosage* | $c_{max,90}$* | $AUC_{90}$** |
|---|---|---|---|---|---|---|
| Eastman HPMCAS-HF | 25 | 0 | 0 | 1820 | | 0 |
| | | 4 | 338 | | | 700 |
| | | 10 | 342 | | | 2,700 |
| | | 20 | 325 | | | 6,100 |
| | | 40 | 352 | | | 12,800 |
| | | 90 | 364 | | 364 | 30,700 |
| | | 1200 | 425 | | | 468,600 |

*μgA/mL
**min · μgA/mL

EXAMPLES 19–21

Tablets containing Drug A were made as follows. An amorphous solid dispersion was prepared as in Example 1. A portion of this dispersion was formed into tablets having the same makeup, but using three different tableting processes. Each tablet consisted of 44.45 wt % dispersion, 49.80 wt % microcrystalline cellulose (AVICEL PH 102, FMC Corporation) 5.0 wt % croscarmellose sodium (AC-DI-SOL, Honeywell & Stein Ltd., Surrey, England), and 0.75 wt % magnesium stearate. The targeted tablet weight was 450 mg, resulting in tablets containing 50 mgA of Drug A.

For Example 19 the dispersion was first granulated by roller compaction on a Freund TF-mini roller compactor using an auger speed of 14 rpm, a roller speed of 2.5 rpm, and a roller pressure of 30 Kg/cm². The resulting compacted material was then milled using a Comill mill at a power setting of 2.5, using Impeller 2A-1607-086 and Screen 2A-045R0377/037. The milled dispersion was then blended in a V-blender with the AVICEL and the AC-DI-SOL for 20 minutes, followed by the addition of magnesium stearate, and final blending for 5 minutes on the V-blender. This blended material was then formed into tablets using 7/16-inch standard round concave (src) tooling on a Kilian T-100 tablet press with precompression of <2 kN and a compression force of 10 kN. A tablet hardness of 12 Kp was achieved.

Example 20 consisted of first blending the SDD in a V-blender with the AVICEL and AC-DI-SOL for 20 minutes, followed by adding a portion (20 wt % of the total) of the magnesium stearate and blending for 5 minutes. The blend was then granulated on a Freund TF-mini roller compactor using an auger speed of 30 rpm, a roller speed of 4 rpm, and a roller pressure of 30 Kg/cm². The resulting compacted material was then milled using a JTmill with a slow power setting and a sieve size of 0.063 inch. The remaining magnesium stearate was added next, and the material was blended for 5 minutes in a V-blender. This material was then formed into tablets using 5/16-inch src tooling on a Kilian T-100 tablet press with a precompression force of 1–2 kN and a compression force of 20 kN.

Example 21 consisted of first blending the dispersion in a V-blender with-the AVICEL and the AC-DI-SOL for 20 minutes, followed by screening through a 10-mesh screen, and adding 20 wt % of the total magnesium stearate and blending for 5 minutes. The blend was then granulated on a Freund TF-mini roller compactor using an auger speed of 30 rpm, a roller speed of 4 rpm, and a roller pressure of 30 Kg/cm². The resulting compacted material was then milled using a JTmill with a "slow" power setting and a sieve size of 0.063 inch. The remaining magnesium stearate was added next, and the material was blended for 5 minutes in a V-blender. This material was then formed into tablets using 7/16-inch src tooling on a Kilian T-100 tablet press with precompression of 1–2 kN and a compression force of 10.7 kN. The resulting tablets had a hardness of 8.5 Kp.

In vitro dissolution was conducted as follows. One tablet was placed in 200 mL of a simulated gastric solution (GB) consisting of 34 mM NaCl and 84 mM HCl for 30 minutes at 37° C. and stirred, and then 50 mL of a simulated intestinal solution comprising 300 mM $KH_2PO_4$, and 620 mM NaOH (IB) was added to produce a final pH of 7.5 and a final volume of 250 mL. Drug concentrations were determined over time by periodically withdrawing samples, centrifuging the samples to remove any undissolved drug, diluting the supernatant in methanol, analyzing the supernatant by HPLC, and calculating drug concentrations. The results are shown in Table 8.

For an in vivo study, dogs that had fasted overnight were dosed with one tablet each and 20 mL of water. Blood was collected from the jugular vein of the dogs before dosing and at various time points after dosing. To 100 μL of each plasma sample, 5 mL of methyl-tert-butyl ether (MTBE) and 1 mL of 500 mM sodium carbonate buffer (pH 9) were added; the sample was vortexed for 1 minute and then centrifuged for 5 minutes. The aqueous portion of the sample was frozen in a dry ice/acetone bath, and the MTBE layer was decanted and evaporated in a vortex evaporator. Dried samples were reconstituted in 100 μl of mobile phase (33% acetonitrile and 67% of 0.1% formic acid in water). Analysis was carried out by HPLC. The results are also shown in Table 8, where $AUC_{0-24}$ is the area under the blood concentration vs. time curve in the first 24 hours.

TABLE 8

| Example No. | In Vitro Drug Released in GB After 20 min | In Vitro Drug Released in GB/IB Test After 60 min | In Vivo $AUC_{0-24}$* |
|---|---|---|---|
| 19 | 30% | 72% | 8.6 |
| 20 | 17% | 42% | 5.3 |
| 21 | 15% | 60% | 5.6 |

*hr · μgA/mL

EXAMPLE 22

Coatings were applied to the tablets of Example 19 using a Freund HCT-30 pan coater. A 4 wt % coating of White OPADRY II (a blend of cellulosic polymer containing $TiO_2$ as a colorant and opacifier from Colorcon, Westpoint, Pa.) and 0.5 wt % coating of Clear OPADRY II (containing no colorant) were applied to the tablets.

EXAMPLE 23

In Vivo Drug Release in a Human

An amorphous solid dispersion containing 25 wt % Drug A and 75 wt % HPMCAS-MF was prepared as in Example 1. The dispersion was used as an oral powder for constitution (OPC) by dissolving it in a solution of 0.02 wt % polyoxyethylene 20 sorbitan monooleate (Tween 80) in sterile water. As a control (Control 3), an OPC was formed using the crystalline form of the drug. A sample of the solid dispersion-containing OPC and of Control 3, each containing 300 mgA of Drug A was taken orally by four healthy human subjects. Blood samples were collected and in vivo drug release profiles were measured as in Example 20. As shown in Table 9, the maximum concentration of drug measured in blood plasma ($c_{max}$) for the solid dispersion-containing OPC was 7-fold that of Control 3, while the $AUC_{0-24}$ was 5-fold that of Control 3, and the time to achieve maximum drug concentration ($t_{max}$) was substantially the same for both formulations.

TABLE 9

| Example No. | Formulation | Dose (mgA) | $c_{max}$ (mg/mL) | $t_{max}$ (hr) | $AUC_{0-24}$ (mg · hr/mL) |
|---|---|---|---|---|---|
| 23 | OPC | 300 | 8.4 ± 1.1 | 2.5 ± 0.6 | 46 ± 7.6 |
| Control 3 | Crystalline OPC | 300 | 1.3 ± 0.3 | 2.3 ± 1.3 | 7.4 ± 3.3 |

EXAMPLE 24

A controlled release tablet was formed using the following procedure. An amorphous solid dispersion was formed as in Example 2, except that the spray solution comprised 2.5 wt % Drug A, 5.0 wt % HPMCAS, and 92.5 wt % acetone and the dispersion contained 33 wt % Drug A. The resulting dispersion was blended with the following tableting excipients for 40 minutes to render the mixture homogeneous, resulting in a final composition of the mixture as follows: 28 wt % of the dispersion, 22 wt % of the tableting aid xylitol containing 1.5 wt % carboxymethyl cellulose, 29 wt % of the hydrogel PEO having an average molecular weight of 600,000 daltons, 20 wt % of the osmopolymer sodium starch glycolate, and 1 wt % of the lubricant magnesium stearate. This homogenous mixture was formed into tablet cores in a tableting press at approximately 4000 psi of compressive force using ¹³⁄₃₂-inch tooling.

The so-formed tablet cores were then coated with a controlled release coating by pan-coating the same with a coating composition comprising 7 wt % cellulose acetate (CA 398-10, Eastman Fine Chemicals, Kingsport, Tenn.), 3 wt % polyethylene glycol (PEG) having an average molecular weight of 3350 daltons, 5 wt % water, and 85 wt % acetone, and then drying the same in a convective oven at 50° C. Five 0.9-mm diameter delivery ports were laser-drilled in the coating of each face for a total of 10 delivery ports for each tablet. The finished weight of individual coated tablets was 500 mg.

EXAMPLE 25

This example illustrates a method for making a dosage form of the present invention with a bilayer core. The bilayer core consists of a drug layer and a sweller layer. To form the drug layer, the following materials may be blended and wet-granulated in a mixer: 50 to 200 g of an amorphous solid dispersion of Drug A; 250 to 325 g of a PEO having an average molecular weight of about 100,000 daltons; 0 to 100 g of a PEO having an average molecular weight of about 200,000 daltons; 10 to 30 g of HPMC having an average molecular weight of about 11,300 daltons; and 0 to 10 g of magnesium stearate. The sweller layer may be formed by wet-granulating the following materials: 110 to 140 g of PEO having an average molecular weight of 5,000,000 to 7,500,000 daltons; 5 to 25 g of an HMPC having a molecular weight of 12,300 daltons; 40 to 70 g sucrose; and 0 to 10 g of magnesium stearate.

The bilayer core is formed by first placing 50 to 300 mg of the sweller layer granulation into the bottom of a die and then lightly tamping the material. On top of this sweller layer is then placed 50 to 300 mg of the drug layer granulation. The two layers are then compressed to a hardness of 6 to 15 Kponds.

The resulting bilayer cores are then coated with a semipermeable coating comprising 50 to 98% CA having an acetyl content of about 32 to 40 wt % and from 2 to 30 wt % PEG having an average molecular weight of about 3,350 daltons. At least one delivery port from 500 to 2,000 μm in diameter is formed in the coating on the drug layer face of the tablet.

EXAMPLE 26

An erodible matrix controlled release device was fabricated using the following procedure. A 1.05 g sample of the amorphous solid dispersion from Example 24 was mixed with 1.70 g HPMC (METHOCEL K 100 LV prem., Dow Chemical, Midland, Mich.), 0.70 g of the lactose filler FAST FLOW (Foremost/Van Water and Rogers, Baaboo, Wis.), and 0.053 g of the lubricant magnesium stearate, all blended for 20 minutes in a TURBULA blender (Willy A. Bachofen AG Muschinenfabrick, Basel, Switzerland) to render the mixture homogeneous. The so-formed homogeneous core mixture contained 10 wt % Drug A, 20 wt % HPMCAS-MF, 48.5 wt % HPMC, 20 wt % lactose, and 1.5 wt % magnesium stearate. This homogeneous mixture was formed into tablets using an F-3 Press (Manesty, Liverpool, England) with ¹¹⁄₃₂-inch tooling. The tablet weight was about 350 mg. As a control (Control 5), a tablet was formed in the same manner, except that 37.4 mg of crystalline drug was used.

EXAMPLE 27

An erodible matrix controlled release device was prepared as follows. First, an amorphous solid dispersion was formed as in Example 2, except that the aqueous-soluble polymer was CAP, the dispersion contained 25 wt % Drug A, and the spray-drying was carried out using a solution of 0.75 wt % Drug A, 2.25 wt % CAP, and 97 wt % acetone, which was fed to a two-fluid nozzle at a pressure of 1.9 bar. To incorporate the dispersion into an erodible matrix, 1.07 g of the same were then mixed with 1.7 g METHOCEL K100, 0.7 g of lactose filler, and 0.05 g of the lubricant magnesium stearate. The tablet weight was 350 mg. A control (Control 6) was formed in the same manner using 26 mg of crystalline Drug A instead of the dispersion.

In vitro dissolution tests were performed for the formulations of Examples 26–27 and Controls 5–6. Dissolution tests were performed by adding the tablet or control to 40 ml of stirred PBS at 37° C. Samples were withdrawn periodically, centrifuged for 1 minute at 13,000 G, diluted in methanol as in Example 12, and the supernatant analyzed by HPLC. Samples were taken periodically, as reported in Table 10, which also shows the data obtained.

TABLE 10

| Example No. | wt % Drug A in Polymer | Polymer | Time (min) | [Drug A]* | AUC** |
|---|---|---|---|---|---|
| 26 | 67 | HPMCAS-MF | 0 | 0.0 | 0 |
|  |  |  | 4 | 0.0 | 0 |
|  |  |  | 10 | 11.2 | 34 |
|  |  |  | 20 | 25.3 | 217 |
|  |  |  | 40 | 52.9 | 999 |
|  |  |  | 90 | 136.3 | 5,730 |
|  |  |  | 120 | 178.3 | 10,449 |
|  |  |  | 180 | 277.7 | 24,131 |
|  |  |  | 240 | 365.6 | 43,432 |
|  |  |  | 360 | 496.8 | 95,177 |
|  |  |  | 525 | 563.2 | 182,625 |
|  |  |  | 720 | 562.9 | 292,415 |
| Control 5 | N/A | None (crystalline drug) | 0 | 0.0 | 0 |
|  |  |  | 4 | 90.1 | 180 |
|  |  |  | 10 | 101.0 | 754 |
|  |  |  | 20 | 98.8 | 1,753 |
|  |  |  | 40 | 166.1 | 4,402 |
|  |  |  | 90 | 147.9 | 12,252 |
|  |  |  | 120 | 164.5 | 16,937 |
|  |  |  | 180 | 137.3 | 25,991 |
|  |  |  | 240 | 141.9 | 34,362 |
|  |  |  | 360 | 161.0 | 52,528 |
|  |  |  | 525 | 179.0 | 80,574 |
|  |  |  | 720 | 157.2 | 113,346 |
| 27 | 75 | CAP | 0 | 0.0 | 0 |
|  |  |  | 10 | 6.8 | 21 |
|  |  |  | 20 | 18.8 | 149 |
|  |  |  | 40 | 46.3 | 799 |
|  |  |  | 90 | 107.9 | 4,654 |
|  |  |  | 120 | 157.8 | 8,640 |
|  |  |  | 180 | 248.4 | 20,826 |
|  |  |  | 240 | 328.5 | 38,131 |
|  |  |  | 360 | 474.7 | 86,322 |
|  |  |  | 525 | 557.0 | 171,442 |
|  |  |  | 720 | 545.3 | 278,918 |
| Control 6 | N/A | None (crystalline drug) | 0 | 0.0 | 0 |
|  |  |  | 10 | 107.8 | 0 |
|  |  |  | 20 | 130.1 | 323 |
|  |  |  | 40 | 109.1 | 1,513 |
|  |  |  | 90 | 118.1 | 3,906 |
|  |  |  | 120 | 121.8 | 9,587 |
|  |  |  | 180 | 151.7 | 13,186 |
|  |  |  | 240 | 170.4 | 21,392 |
|  |  |  | 360 | 135.3 | 31,055 |
|  |  |  | 525 | 134.8 | 49,395 |
|  |  |  | 720 | 168.3 | 73,701 |

*μgA/mL
**min · μgA/mL

EXAMPLES 28–30

These examples disclose simple physical mixtures of Drug A and a concentration-enhancing polymer. Mixtures of Drug A and HPMCAS-MF were formed by dry mixing amorphous Drug A with HPMCAS-MF. For Example 28, the composition comprised 3.6 mg (75 wt %) Drug A and 1.2 mg (25 wt %) HPMCAS-MF; for Example 29, the composition comprised 3.6 mg (50 wt %) Drug A and 3.6 mg (50 wt %) HPMCAS-MF; for Example 30, the composition comprised 3.6 mg (25 wt %) Drug A and 10.8 mg (75 wt %) HPMCAS-MF.

These compositions were evaluated in in vitro dissolution tests using the procedures outlined in Example 12. The quantities of drug and polymer noted above were each added to a microcentrifuge tube, to which was added 1.8 ml of PBS solution. The tube was vortexed immediately after adding the PBS solution. The results of these dissolution tests are given in Table 11, and summarized in Table 12.

TABLE 11

| Example | Time (mins) | Drug A Concentration (μg/mL) | AUC (min*μg/mL) |
|---|---|---|---|
| 28 | 0 | 0 | 0 |
| 75 wt % | 4 | 714 | 1,400 |
| Drug A/ | 10 | 737 | 5,800 |
| 25 wt % HPMCAS- | 20 | 696 | 12,900 |
| MP | 40 | 690 | 26,800 |
|  | 90 | 729 | 62,300 |
|  | 180 | 684 | 125,800 |
|  | 1200 | 440 | 711,100 |
| 29 | 0 | 0 | 0 |
| 50 wt % | 4 | 377 | 755 |
| Drug A/ | 10 | 370 | 3,000 |
| 50 wt % HPMCAS- | 20 | 836 | 9,000 |
| MF | 40 | 846 | 25,800 |
|  | 90 | 898 | 69,500 |
|  | 180 | 918 | 151,200 |
|  | 1200 | 627 | 915,800 |
| 30 | 0 | 0 | 0 |
| 25 wt % | 4 | 999 | 2,000 |
| Drug A/ | 10 | 1030 | 8,100 |
| 75 wt % HPMCAS- | 20 | 1065 | 18,600 |
| MF | 40 | 1133 | 40,600 |
|  | 90 | 1185 | 98,500 |
|  | 180 | 1304 | 210,500 |
|  | 1200 | 1379 | 1,521,500 |

TABLE 12

| Example | Dosage (μg/mL) | $C_{max,90}$ (μg/mL) | $AUC_{90}$ (min*μg/mL) | $C_{1200}$ (μg/mL) |
|---|---|---|---|---|
| 28 | 2000 | 729 | 62,300 | 440 |
| 29 | 2000 | 898 | 69,500 | 627 |
| 30 | 2000 | 1185 | 98,500 | 1379 |
| Control 2 | 2000 | 586 | 20,600 | 203 |

These simple physical mixtures of amorphous Drug A and HPMCAS-MF showed much better performance than the amorphous drug alone (Control 2, shown in Table 12 for comparison), with $C_{max,90}$ values that were 1.24- to 2.0-fold that of Control 2, and $AUC_{90}$ values that were 3.0- to 4.8-fold that of Control 2.

EXAMPLE 31

A composition was formed by blending 50 wt % of the composition of Example 2 (containing 50 wt % Drug A and 50 wt % HPMCAS-MF) with 50 wt % HPMCAS-MF. This composition was evaluated in a dissolution test as described in Example 12. The results of this test are presented in Table 13, and show that the blend of the amorphous solid dispersion of Drug A with polymer performs well, with a $C_{max,90}$ value that is 6.6-fold that of the crystalline drug alone (Control 1) and an $AUC_{90}$ value that is 6.2-fold that of Control 1.

| Example | Time (min) | Drug A Concentration (μg/mL) | AUC (min*μg/mL) |
|---|---|---|---|
| 31 | 0 | 0 | 0 |
|  | 4 | 766 | 1,500 |
|  | 10 | 840 | 6,400 |

-continued

| Example | Time (min) | Drug A Concentration (μg/mL) | AUC (min*μg/mL) |
|---|---|---|---|
| | 20 | 874 | 14,900 |
| | 40 | 884 | 32,500 |
| | 90 | 979 | 79,100 |
| | 1200 | 1133 | |

EXAMPLES 32–35

An amorphous solid dispersion of 50 wt % Drug A and 50 wt % polymer was made by first mixing Drug A in a solvent together with HPMCAS-MF to form a solution. The solution comprised 7.5 wt % Drug A, 7.5 wt % HPMCAS, 80.75 wt % acetone and 4.25 wt % water. This solution was then spray-dried by directing an atomizing spray using a two-fluid external-mix spray nozzle at 2.7 bar (37 psig) at a feed rate of 175 g/min into the stainless-steel chamber of a Niro spray-dryer, maintained at a temperature of 175° C. at the inlet and 70° C. at the outlet.

The resulting amorphous solid spray-dried dispersion (SDD) was collected via a cyclone and then dried in a Gruenberg solvent tray-dryer by spreading the spray-dried particles onto polyethylene-lined trays to a depth of not more than 1 cm and then drying them at 40° C. for 16 hours.

The SDD above was incorporated into tablets containing 25, 50, 100, and 200 mg. Tablets with a dose of 25 mg (Example 32) consisted of 7.14 wt % SDD, 40.0 wt % HPMCAS-MF, 49.11 wt % microcrystalline cellulose (Avicel® PH 102), 3.0 wt % croscarmellose sodium (Ac-Di-Sol®), and 0.75 wt % magnesium stearate. Tablets with a dose of 50 mg (Example 33) consisted of 14.29 wt % SDD, 40.0 wt % HPMCAS-MF, 41.96 wt % Avicel® PH 102, 3.0 wt % Ac-Di-Sol®, and 0.75 wt % magnesium stearate. Tablets with a dose of 100 mg (Example 34) consisted of 28.57 wt % SDD, 30.0 wt % HPMCAS-MF, 37.68 wt % Avicel® PH 102, 3.0 wt % Ac-Di-Sol®, and 0.75 wt % magnesium stearate. Tablets with a dose of 200 mg (Example 35) consisted of 57.14 wt % SDD, 39.11 wt % Avicel® PH 102, 3.0 wt % Ac-Di-Sol®, and 0.75 wt % magnesium stearate. In each case, the target tablet weight was 700 mg.

To form the tablets, the SDD was first granulated (roller compacted) on a Freund TF-mini roller compactor using an auger speed of 30 rpm, a roller speed of 4 rpm, and a roller pressure of 30 Kg$_f$/cm². The resulting compacted material was then reduced using a mini-Comil at a power setting of 4, with sieve 039R. The milled SDD was then blended in a V-blender with the HPMCAS-MF, Avicel®, and Ac-Di-Sol® for 20 minutes using the proportions noted above. Next, a portion of the magnesium stearate (about 20 wt % of the total magnesium stearate used) was added and the material was blended for 5 minutes. The blend was then granulated again using an auger speed of 20 rpm, a roller speed of 4 rpm, and a roller pressure of 30 Kg$_f$/cm². The resulting compacted material was then reduced using a Comill with a power setting of 3 and a sieve size of 032R. The remaining magnesium stearate was then added, and the material was blended for 5 minutes in a V-blender. This material was then formed into tablets using 0.3437×0.6875-inch oval tooling on a Kilian T-100 tablet press with pre-compression of 1 to 2 kN and a compression force of 10 kN.

To test in vitro drug dissolution, one of each of the tablets was placed in 200 mL of a gastric buffer solution (0.1 N HCl, pH 1.2) for 30 minutes at 37° C. and stirred, after which 50 mL of a pH 13 buffer solution was added to produce a final pH of 7.5 and a final volume of 250 mL. The drug concentration was determined over time by periodically withdrawing samples, centrifuging the samples to remove any undissolved drug, diluting the supernatant in methanol, analyzing the samples by HPLC, and calculating drug concentrations. The concentrations of drug obtained in these in vitro dissolution tests are shown in Table 14 below.

TABLE 14

| Example | Time (min) | Drug A Concentration (μg/mL) | AUC (min*μg/mL) |
|---|---|---|---|
| 32 | 0 | 0 | 0 |
| 25 mg | 5 | 6 | 16 |
| | 15 | 13 | 110 |
| | 20 | 15 | 178 |
| | 35 | 25 | 478 |
| | 45 | 30 | 755 |
| | 60 | 36 | 1,300 |
| | 75 | 43 | 1,800 |
| | 90 | 50 | 2,500 |
| | 120 | 58 | 4,200 |
| | 180 | 65 | 7,900 |
| | 1200 | 96 | 90,200 |
| 33 | 0 | 0 | 0 |
| 50 mg | 5 | 9 | 24 |
| | 15 | 19 | 166 |
| | 20 | 23 | 271 |
| | 35 | 42 | 755 |
| | 45 | 61 | 1,300 |
| | 60 | 82 | 2,300 |
| | 75 | 99 | 3,700 |
| | 90 | 111 | 5,300 |
| | 120 | 130 | 8,900 |
| | 180 | 152 | 17,400 |
| | 1200 | 202 | 197,800 |
| 34 | 0 | 0 | 0 |
| 100 mg | 5 | 20 | 49 |
| | 15 | 43 | 361 |
| | 20 | 50 | 594 |
| | 35 | 112 | 1,800 |
| | 45 | 150 | 3,100 |
| | 60 | 186 | 5,700 |
| | 75 | 199 | 8,500 |
| | 90 | 213 | 11,600 |
| | 120 | 236 | 18,300 |
| | 180 | 260 | 33,200 |
| | 1200 | 381 | 360,300 |
| 35 | 0 | 0 | 0 |
| 200 mg | 5 | 26 | 64 |
| | 15 | 64 | 514 |
| | 20 | 81 | 878 |
| | 35 | 168 | 2,800 |
| | 45 | 424 | 5,700 |
| | 60 | 470 | 12,400 |
| | 75 | 479 | 19,500 |
| | 90 | 502 | 26,900 |
| | 120 | 518 | 42,200 |
| | 180 | 522 | 73,400 |
| | 1200 | 298 | 491,000 |

The data demonstrate that approximately all of Drug A had been released by 1200 minutes.

EXAMPLE 36

This example illustrates a method for making a tablet dosage form of the present invention containing an amorphous dispersion of Drug A. An amorphous solid dispersion of Drug A and HPMCAS was made by mixing Drug A in a solvent together with HPMCAS to form a solution, and then spray-drying the solution. The solution comprised 7.5 wt % Drug A, 7.5 wt % HPMCAS-MF, 4.25 wt % water, and 80.75 wt % acetone. The solution was then spray-dried by directing an atomizing spray using a two-fluid external-mix spray nozzle at 2.7 bar at a feed rate of 175 g/min into the stainless steel chamber of a Niro spray-dryer, maintained at a temperature of 140° C. at the inlet and 50° C. at the outlet. The resulting SDD was collected via a cyclone and then dried in a Gruenberg solvent tray-dryer by spreading the spray-dried particles onto polyethylene-lined trays to a depth of not more than 1 cm and then drying them at 40° C. for at least 8 hours. After drying, the SDD contained 50 wt % Drug A.

The tablets contained 50 wt % SDD, 25 wt % anhydrous dibasic calcium phosphate, 12 wt % Avicel® PH 200, 12.5 wt % crospovidone, and 0.5 wt % magnesium stearate. The total batch weight was 190 g. The ingredients except for magnesium stearate were added to a Turbula blender and blended for 20 minutes. Next, half of the magnesium stearate was added and blended for 5 minutes. The blend was then roller-compacted with a Vector TF mini roller compactor using an auger speed of 30 rpm, a roller speed of 5 rpm, and a roller pressure of 35.2 Kgf/cm². The resulting compacted material was then milled using a Quadro Comil 193AS mill at a power setting of 3, using impeller 2B-1607-005 and Screen 2B-075R03151173. The second half of the magnesium stearate was added next, and the material was blended for 5 minutes in a Turbula blender. This material was then formed into 800 mg tablets using ½-inch SRC tooling on a Manesty F press. An average tablet hardness of 19 Kp was obtained. Average disintegration time in deionized water (USP disintegration apparatus) was 2 minutes, 50 seconds.

EXAMPLE 37

The tablets of Example 36 were coated in the LDCS 20 pan-coater using an 8 wt % aqueous solution of Opadry® II Clear. The following coating conditions were used: tablet bed weight, 900 g; pan speed, 20 rpm; outlet temperature, 40° C.; solution flow, 8 g/min; atomization pressure, 20 psi; and air flow, 40 cfm. The coating weight gain was 3 wt %. The resulting average coated tablet hardness was 45 Kp. Average disintegration time in deionized water was 4 minutes, 57 seconds.

EXAMPLE 38

This example illustrates another method for making a tablet dosage form of the present invention containing an amorphous dispersion of Drug A. An amorphous solid dispersion of Drug A and HPMCAS was made by mixing Drug A in a solvent together with HPMCAS to form a solution, and then spray-drying the solution, as described in Example 36. The tablets contained 50 wt % of the SDD, 25 wt % anhydrous dibasic calcium phosphate, 12 wt % Avicel® PH 105 QS, 12.5 wt % crospovidone, and 0.5 wt % magnesium stearate. To form the tablets, the ingredients, except magnesium stearate, were first added to a V-blender and blended for 20 minutes, followed by de-lumping using a 10-mesh screen. Next, half of the magnesium stearate was added and blended for 5 minutes. The blend was then roller compacted with a Vector TF mini roller compactor, fitted with "S"-type rolls, using an auger speed of 30 rpm, a roller speed of 4 rpm, and a roller pressure of 30 Kgf/cm². The resulting compacted material was then milled using a Fitzpatrick M5A mill at a power setting of 350 rpm, with a sieve size of 16 mesh. The second half of the magnesium stearate was added next, and the material was blended for 5 minutes in a V-blender. This material was then formed into 800 mg tablets using ½-inch SRC tooling on a Killian T-100 (feeder frame speed 30 rpm, 30,000 tablets/hour) and compressed to a hardness of 25 Kp.

The so-formed tablets were coated in a Freund HCT-30 pan-coater using an aqueous solution of 3.5 wt % Opadry® II White and 0.5 wt % Opadry® II Clear. The following coating conditions were used: tablet bed weight, 1000 g; pan speed, 17 rpm; outlet temperature, 42° C.; and solution flow, 6 g/min. Average disintegration time in deionized water was <5 minutes.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

The invention claimed is:

1. A process for forming a pharmaceutical composition, comprising the steps of:
    (a) forming solid amorphous dispersion particles each comprising a sparingly soluble drug and a concentration enhancing polymer, wherein at least a major portion of said drug is amorphous;
    (b) blending said solid amorphous dispersion particles and matrix material to form a blend;
    (c) feeding said blend to a melt-congeal process to form a molten mixture comprising said solid amorphous dispersion particles and said matrix material; and
    (d) cooling said molten mixture and forming solid particles each comprising said solid amorphous dispersion particles trapped within said matrix material.

2. The process of claim 1, wherein said matrix material is selected from the group consisting of hydrogenated and partially hydrogenated vegetable oils; mono-, di-, and triglycerides of fatty acids; propylene glycol and ethylene glycol mono- and di-esters of fats and fatty acids; waxes; and long chain alcohols.

3. The process of claim 1 wherein said solid amorphous dispersion particles are formed by a process selected from the group consisting of melt fusion, melt congealing, lyophilization, trituration, extrusion, milling, and solvent processing.

4. The process of claim 3 wherein said solid amorphous dispersion particles are formed by spray-drying a solution comprising said sparingly soluble drug, said concentration-enhancing polymer, and a solvent.

5. The process of any one of claims 4, wherein said solution further comprises an additional excipient selected from the group consisting of a surfactant, a water-swellable polymer, a water-soluble polymer, and a hydrophobic solute.

6. The process of any one of claims 1–4 wherein said concentration-enhancing polymer is selected from the group consisting of hydroxypropyl methyl cellulose acetate, hydroxypropyl methyl cellulose, hydroxypropyl cellulose, methyl cellulose, hydroxyethyl methyl cellulose, hydroxyethyl cellulose acetate, hydroxyethyl ethyl cellulose, hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyndinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

7. The process of any one of claims 1–4 wherein said solid amorphous dispersion particles provide concentration-enhancement in a use environment relative to a control composition consisting of crystalline drug without any concentration-enhancing polymer, said concentration-enhancing polymer being at least one of:
   (i) a maximum dissolved drug concentration in said use environment that is at least 1.25-fold that provided by said control composition; and
   (ii) a dissolved drug concentration versus time curve (AUC) for any period of at least 90 minutes between the time of introduction into the use environment and about 270 minutes following introduction into the use environment that is at least 1.25-fold that provided by said control composition.

8. The process of any one of claims 1–4 wherein said solid amorphous dispersion particles provide improved relative bioavailability relative to a control composition consisting of crystalline drug without any concentration-enhancing polymer.

9. The product of the processes of any one of claim 1–4.

* * * * *